United States Patent
Koch et al.

(12) 
(10) Patent No.: US 6,291,450 B1
(45) Date of Patent: *Sep. 18, 2001

(54) CARBOXYLIC ACID SUBSTITUTED HETEROCYCLES, DERIVATIVES THEREOF AND METHODS OF USE

(75) Inventors: Kevin Koch, Boulder, CO (US); Andreas Termin, Encinitas, CA (US); John A. Josey, Longmont, CO (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/588,978

(22) Filed: Jun. 7, 2000

Related U.S. Application Data

(62) Division of application No. 09/213,031, filed on Dec. 16, 1998
(60) Provisional application No. 60/068,200, filed on Dec. 19, 1997.

(51) Int. Cl.[7] ..................... C07D 401/00; C07D 223/06; A61K 31/55
(52) U.S. Cl. ............................... 514/217.03; 514/217.04; 514/217.05; 514/217.06; 514/217.07; 514/217.08; 514/217.09; 514/217.1; 514/217.11; 540/596; 540/597; 540/598; 540/599; 540/600; 540/601; 540/602; 540/603; 540/604
(58) Field of Search ..................... 540/596, 604, 540/597, 598, 599, 600, 601, 602, 603

(56) References Cited

FOREIGN PATENT DOCUMENTS

| | | |
|---|---|---|
| 039051 | 11/1981 | (EP) . |
| 606046 | 7/1994 | (EP) . |
| 803505 | 10/1997 | (EP) . |
| WO 96/29313 | 9/1996 | (WO) . |
| WO 96/33172 | 10/1996 | (WO) . |
| WO 97/18194 | 5/1997 | (WO) . |

OTHER PUBLICATIONS

Gibson et al., J Org. Chem., 59:3216 (1994).
Svensson et al., Drug Metabolism Reviews, 19(2), 165–194 (1988).
Bundgaard, J. Med. Chem., 32(12), 2503 (1989).
Baldwin et al., Tetrahedron, 45(19), 6309 (1989).
Schuster et al., Angew. Chem. Int. Ed. Engel, 36:2036–2056 (1997).
Ninomiya et al., Tetrahedron, 30:2151 (1974).
Wadsworth, Organic Reactions, 25:73–253 (1977).
Rabjohn, Organic Reactions, 24:261–415 (1976).
Nagasawa et al., J. Med. Chem., 14(6), 501–508 (1971).

*Primary Examiner*—Bruck Kifle
(74) *Attorney, Agent, or Firm*—Frank S. Ungemach; Stuart L. Watt

(57) ABSTRACT

Selected novel carboxylic acid substituted heterocycle compounds are effective for prophylaxis and treatment of inflammation, tissue degradation, cancer, fibrosis and related diseases. The invention encompasses novel compounds, analogs, prodrugs and pharmaceutically acceptable salts thereof, pharmaceutical compositions and methods for prophylaxis and treatment of inflamation, tissue degradation and related diseases. The subject invention also relates to processes for making such compounds as well as to intermediates useful in such processes.

12 Claims, No Drawings

CARBOXYLIC ACID SUBSTITUTED HETEROCYCLES, DERIVATIVES THEREOF AND METHODS OF USE

This application is a division of application Ser. No. 09/213,031 filed Dec. 16, 1998, which claims the benefit of Provisional Application Serial No. 60/068,200, Filed Dec. 19, 1997, which are hereby incorporated by reference.

BACKGROUND OF THE INVENTION

The present invention relates to metalloproteinase inhibitors and, more particularly, relates to novel compounds, compositions and methods for prophylaxis and treatment of inflammation, tissue degradation and the like. This invention, in particular, relates to novel carboxylic acid substituted heterocyclic compounds, compositions containing such compounds and methods of use of such compounds. The subject invention also relates to processes for making such compounds as well as to intermediates useful in such processes.

Metalloproteinase enzymes, such as collagenases, stromelysins and gelatinases, may contribute to the onset or etiology of, or exacerbate disease states which are related to, connective tissue degradation and the like. For example, matrix metalloproteinases, such as collagenases, stromelysins and gelatinases, are thought to be involved in the tissue breakdown observed in rheumatoid arthritis; osteoarthritis; osteopenias (e.g., osteoporosis); periodontitis; gingivitis; corneal, epidermal and gastric ulceration; and tumour metastasis, invasion and growth; in neuroinflammatory disorders, such as myelin degradation (e.g., multiple sclerosis); and in angiogenesis dependent diseases, such as arthritic conditions; cancer; solid tumor growth; psoriasis; proliferative retinopathies; neovascular glaucoma; ocular tumours; angiofibromas; hemangiomas; nephritis; pulmonary inflammation; and restenosis.

WO 96/33172 discloses N-arylsulfonyl and N-heteroarylsulfonyl substituted 6 membered ring heterocycle hydroxamic acid derivatives, such as N-arylsulfonyl- and N-heteroarylsulfonyl-piperidinyl-2-hydroxamic acid compounds, and their preparation and use as inhibitors of matrix metalloproteinases and TNF production.

EP 606046 discloses N-arylsulfonyl and N-heteroarylsulfonyl substituted 5–6 membered ring heterocycle hydroxamic acid derivatives, such as N-arylsulfonyl- and N-heteroarylsulfonyl-piperidinyl-2-hydroxamic acid compounds and N-arylsulfonyl- and N-heteroarylsulfonyl-1,2,3,4-tetrahydroisoquinolinyl-2-hydroxamic acid compounds, preparation and use as inhibitors of matrix metalloproteinases.

WO 97/18194 discloses certain cyclic and heterocyclic N-substituted α-substituted iminohydroxamic and carboxylic acids, and their preparation and use as inhibitors of matrix metalloproteinases.

EP 803505 discloses optionally substituted aryl fused N-heterocycles and their preparation and use as inhibitors of metalloproteinases.

BRIEF DESCRIPTION OF THE INVENTION

The present invention relates to selected metalloproteinase inhibitory compounds, analogs and pharmaceutically acceptable salts and prodrugs thereof. The subject compounds are characterized as carboxylic acid substituted heterocyclic compounds. The compounds are useful in the prophylaxis and treatment of inflammation, tissue degradation and related diseases. Therefore, this invention also encompasses pharmaceutical compositions and methods for prophylaxis and treatment of inflamation, tissue degradation and related diseases. The subject invention also relates to processes for making such compounds, as well as to intermediates useful in such processes.

DETAILED DESCRIPTION OF THE INVENTION

In accordance with the present invention, there is provided a compound of the Formula I below:

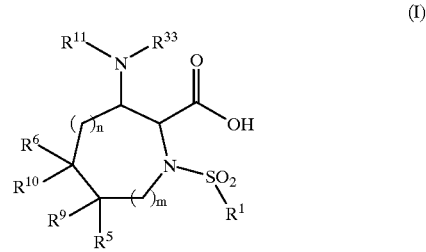

(I)

or a pharmacutically acceptable salt thereof, wherein
m is 1 or 2; and n is 0, 1 or 2;
$R^1$ is (1) an alkyl, alkenyl, alkynyl, cycloalkyl or heterocyclyl radical optionally substituted by 1–3 radicals of —OH, —$OR^3$, —$SR^3$, —$S(O)R^3$, —$S(O)_2R^3$, —$C(O)R^3$, —$NR^3R^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)R^3$, —$S(O)_2R^3$, —$C(O)R^3$, —$NR^3R^4$, amino, alkanoylamino, alkylsulfonylamino, alkoxycarbonylamino, alkoxycarbonyl, cyano, halo, azido, alkyl or haloalkyl;
preferably, $R^1$ is (1) an $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH, —$OR^3$, $SR^3$, —$S(O)R^3$, —$S(O)_2R^3$, —$C(O)R^3$, —$NR^3R^4$, aryl, heteroaryl, cycloalkyl or heterocyclyl; or ((2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)R^3$, —$S(O)_2R^3$, —$C(O)R^3$, —$NR^3R^4$, amino, $C_1$–$C_8$ alkanoylamino, $C_1$–$C_8$ alkylsulfonylamino, $C_1$–$C_8$ alkoxycarbonylamino, $C_1$–$C_8$ alkoxycarbonyl, cyano, halo, azido, $C_1$–$C_8$ alkyl or $C_1$–$C_8$ haloalkyl of 1–3 halo radicals;

more preferably, $R^1$ is (1) a $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$—SR$^3$, —S(O)R$^3$, —S(O)$_2$R$^3$, —C(O)R$^3$, —NR$^3$R$^4$, amino, $C_1$–$C_4$ alkanoylamino, $C_1$–$C_4$ alkylsulfonylamino, $C_1$–$C_4$ alkoxycarbonylamino, $C_1$–$C_4$ alkoxycarbonyl, cyano, halo, azido, $C_1$–$C_6$ alkyl or $C_1$–$C_4$ haloalkyl of 1–3 halo radicals;

more preferably, $R^1$ is (1) a $C_1$–$C_{12}$ alkyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —CF$_3$ radicals;

more preferably, $R^1$ is (1) an $C_1$–$C_{12}$ alkyl radical optionally substituted by 1–3 radicals of —OH, —OR$^3$, —SR$^3$, —S(O)$_2$R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —CF$_3$ radicals;

more preferably, $R^1$ is (1) an $C_1$–$C_4$ alkyl radical substituted by 1–2 radicals of —OH, —OR$^3$, —NR$^3$R$^4$, aryl or heteroaryl; or (2) an aryl radical optionally substituted by a monocyclic heteroaryl radical of 5–6 ring members; or (3) a heteroaryl radical optionally substituted by a phenyl radical; wherein the phenyl, aryl and heteroaryl radicals of (1), (2) and (3) are optionally substituted by 1–2 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —CF$_3$ radicals;

more preferably, $R^1$ is aryl or heteroaryl radicals optionally substituted by 1–2 radicals of hydroxy, —OR$^3$, —SR$^3$, —S(O)$_2$R$^3$, —NR$^3$R$^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —CF$_3$ radicals; and more preferably, $R^1$ is an aryl radical optionally substituted by 1–2 radicals of hydroxy, —OR$^3$, —S(O)$_2$R$^3$, —NR$^3$R$^4$, amino, acetylamino, methylsulfonylamino, halo, $C_1$–$C_4$ alkyl or —CF$_3$ radicals;

more preferably, $R^1$ is a phenyl or biphenyl radical optionally substituted by 1–2 radicals of hydroxy, —OR$^3$, —S(O)$_2$R$^3$, —NR$^3$R$^4$, amino, acetylamino, methylsulfonylamino, halo, $C_1$–$C_4$ alkyl or —CF$_3$ radicals;

most preferably, $R^1$ is a phenyl or biphenyl radical optionally substituted by 1–2 radicals of hydroxy, —OR$^3$, halo, methyl or —CF$_3$ radicals; and provided that the total number of phenyl, aryl, heteroaryl, cycloalkyl and heterocyclyl radicals in $R^1$ is preferably 0–3, more preferably, 0–2, most preferably, 1–2;

wherein each $R^3$ is independently an alkyl, haloalkyl, aryl, heteroaryl, aryl-alkyl or heteroaryl-alkyl radical, wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy;

preferably, each $R^3$ is independently a $C_1$–$C_8$ alkyl, $C_1$–$C_8$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals;

more preferably, each $R^3$ is independently a $C_1$–$C_4$ alkyl, $C_1$–$C_4$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^3$ is independently an $C_1$–$C_4$ alkyl, —CF$_3$, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —CF$_3$ or —OCF$_3$;

more preferably, each $R^3$ is independently a $C_1$–$C_4$ alkyl, —$CF_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —$CF_3$ or —$OCF_3$;

more preferably, each $R^3$ is independently a $C_1$–$C_4$ alkyl, —$CF_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_2$ alkoxy, $C_1$–$C_2$ alkylthiol, amino, acetylamino, methylsulfonylamino, $C_1$–$C_2$ alkylsulfonyl, $C_1$–$C_4$ alkoxycarbonylamino, $C_1$–$C_4$ alkoxycarbonyl, halo, $C_1$–$C_2$ alkyl, —$CF_3$ or —$OCF_3$;

more preferably, each $R^3$ is independently a $C_1$–$C_4$ alkyl, —$CF_3$, aryl, heteroaryl, arylmethyl or heteroarylmethyl radical;

more preferably, each $R^3$ is independently an $C_1$–$C_4$ alkyl, —$CF_3$, phenyl, heteroaryl, phenylmethyl or heteroarylmethyl radical;

most preferably, each $R^3$ is independently an methyl, —$CF_3$, phenyl, heteroaryl, phenylmethyl or heteroarylmethyl radical; and each $R^4$ is independently a hydrogen or alkyl radical; preferably, each $R^4$ is independently a hydrogen or $C_1$–$C_8$ alkyl radical; more preferably, each $R^4$ is independently a hydrogen or $C_1$–$C_4$ alkyl radical; most preferably, each $R^4$ is independently a hydrogen or methyl radical; and $R^{11}$ is a —$C(O)$—$R^{31}$, —$C(O)$—$OR^{30}$, —$C(O)$—$NR^{32}R^{31}$, —$S(O)_2$—$R^{30}$ or —$S(O)_2$—$NR^{32}R^{31}$ radical; preferably, $R^{11}$ is a —$C(O)$—$R^{31}$ or —$S(O)_2$—$R^{30}$ or —$S(O)_2$—$NR^{32}R^{31}$ radical;

wherein $R^5$ and $R^6$ are each independently a hydrogen or alkyl radical; preferably, $R^5$ and $R^6$ are each independently a hydrogen or $C_1$–$C_4$ alkyl radical; and more preferably, $R^5$ and $R^6$ are each a hydrogen radical; or $CR^5$—$CR^6$ is C=C (double bonded carbon atoms);

wherein $R^9$ and $R^{10}$ are each independently —B—A, provided that the combined total number of aryl, heteroaryl, cycloalkyl and heterocyclyl radicals in $R^9$, $R^{10}$ and $R^{11}$ is 0–3, preferably, 0–2;

wherein each B is independently a (1) bond; (2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio, cyano or halo, and/or (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy; (3) heterocyclyl radical optionally substituted by 1–3 radicals of amino, alkylamino, dialkylamino, alkanoylamino, alkoxycarbonyl amino, alkylsulfonylamino, hydroxy, alkoxy, alkylthio, cyano, alkyl, haloalkyl or haloalkoxy; or (4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy;

preferably, each B is independently a (1) bond; (2) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano or halo, and/or (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkyl sulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals; (3) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (4) aryl or heteroaryl radical optionally substituted by 1–3 radicals of amino, $C_1$–$C_4$ alkylamino, di-($C_1$–$C_4$ alkyl)-amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_8$ haloalkyl of 1–3 halo radicals or $C_1$–$C_8$ haloalkoxy of 1–3 halo radicals;

more preferably, each B is independently a (1) bond; (2) $C_1$–$C_8$ alkyl radical optionally substituted by (a) a radical of amino, $C_1$–$C_4$ alkylamino, di-($C_1$–$C_4$ alkyl)-amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ halo alkoxy of 1–3 halo radicals; (3) heterocyclyl radical; or (4) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;

more preferably, each B is independently a (1) bond; (2) $C_1$–$C_8$ alkyl radical optionally substituted by (a) a radical of amino, $C_1$–$C_4$ alkylamino, di-($C_1$–$C_4$ alkyl)-amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkyl thio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals; (3) heterocyclyl radical; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkyl sulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

more preferably, each B is independently a (1) bond; (2) $C_1$–$C_4$ alkyl radical optionally substituted by (a) a radical of amino, $C_1$–$C_2$ alkylamino, di-($C_1$–$C_2$ alkyl)-amino, $C_1$–$C_2$ alkanoylamino, ($C_1$–$C_4$ alkoxy)carbonylamino, hydroxy, $C_1$–$C_2$ alkoxy, and/or (b) 1–2 halo radicals, and/or (c) a radical of heterocyclyl, aryl or heteroaryl optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals; (3) heterocyclyl radical; or (4) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy) carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals;

more preferably, each B is independently a (1) bond or $C_1$–$C_4$ alkyl radical; or (2) aryl or heteroaryl radical optionally substituted by a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals; and most preferably, each B is independently a bond, $C_1$–$C_4$ alkyl, aryl or heteroaryl radical;

wherein each A is independently a (1) hydrogen radical; (2) halo, cyano or nitro radical; (3) —C(O)—$R^{30}$, —C(O)—$OR^{31}$, —C(O)—$NR^{32}R^{31}$ or —C($NR^{32}$)—$NR^{32}R^{31}$ radical; (4) —$OR^{31}$, —O—C(O)—$R^{31}$, —O—C(O)—$NR^{32}R^{31}$ or —O—C(O)—$NR^{33}$—S(O)$_2$—$R^{30}$ radical; (5) —$SR^{31}$, —S(O)—$R^{30}$, —S(O)$_2$—$R^{30}$, —S(O)$_2$—$NR^{32}R^{31}$, —S(O)$_2$—$NR^{33}$—C(O)—$R^{31}$, —S(O)$_2$—$NR^{33}$—C(O)—$OR^{30}$ or —S(O)$_2$—$NR^{33}$—C(O)—$NR^{32}R^{31}$ radical; or (6) —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$, —$NR^{33}$—C($NR^{32}$)—$NR^{32}R^{31}$, —$NR^{33}$—S(O)$_2$—$R^{30}$ or —$NR^{33}$—S(O)$_2$—$NR^{32}R^{31}$ radical;

preferably, each A is independently a (1) hydrogen radical; (2) halo, cyano or nitro radical; (3) —C(O)—$R^{30}$, —C(O)—$OR^{31}$, —C(O)—$NR^{32}R^{31}$ or —C($NR^{32}$)—$NR^{32}R^{31}$ radical; (4) —$OR^{31}$, —O—C(O)—$R^{31}$, —O—C(O)—$NR^{32}R^{31}$ or —O—C(O)—$NR^{33}$—S(O)$_2$—$R^{30}$ radical; (5) —$SR^{31}$, —S(O)—$R^{30}$, —S(O)$_2$—$R^{30}$, —S(O)$_2$—$NR^{32}R^{31}$, —S(O)$_2$—$NR^{33}$—C(O)—$R^{31}$, —S(O)$_2$—$NR^{33}$—C(O)—$OR^{30}$ or S(O)$_2$—$NR^{33}$—C(O)—$NR^{32}R^{31}$ radical; or (6) —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$, —$NR^{33}$—C($NR^{32}$)—$NR^{32}R^{31}$, —$NR^{33}$—S(O)$_2$—$R^{30}$ or —$NR^{33}$—S(O)$_2$—$NR^{32}R^{31}$ radical;

more preferably, each A is independently a hydrogen, halo, cyano, nitro, —C(O)—$R^{30}$, —C(O)—$OR^{31}$, —C(O)—$NR^{32}R^{31}$, —C($NR^{32}$)—$NR^{32}R^{31}$, —$OR^{31}$, —O—C(O)—$R^{31}$, —O—C(O)—$NR^{32}R^{31}$, —$SR^{31}$, —S(O)—$R^{30}$, —S(O)$_2$—$R^{30}$, —S(O)$_2$—$NR^{32}R^{31}$, —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$, —$NR^{33}$—C($NR^{32}$)—$NR^{32}R^{31}$, —$NR^{33}$—S(O)$_2$—$R^{30}$ or —$NR^{33}$—S(O)$_2$—$NR^{32}R^{31}$ radical;

more preferably, each A is independently a hydrogen, halo, —C(O)—$R^{30}$, —C(O)—$OR^{31}$, —C(O)—$NR^{32}R^{31}$, —C($NR^{32}$)—$NR^{32}R^{31}$, —$OR^{31}$, —$SR^{31}$, —S(O)$_2$—$R^{30}$, —S(O)$_2$—$NR^{32}R^{31}$, —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$, —$NR^{33}$—S(O)$_2$—$R^{30}$ or —$NR^{33}$—S(O)$_2$—$NR^{32}R^{31}$ radical;

more preferably, each A is independently a hydrogen, halo, —C(O)—$R^{30}$, —C(O)—$NR^{32}R^{31}$, —C($NR^{32}$)—$NR^{32}R^{31}$, —$OR^{31}$, —$SR^{31}$, —S(O)$_2$—$R^{30}$, —S(O)$_2$—$NR^{32}R^{31}$, —$NR^{32}R^{31}$, —$NR^{33}$—C(O)—$R^{31}$ or —$NR^{33}$—S(O)$_2$$R^{30}$ radical; and most preferably, each A is independently a hydrogen, halo, —C(O)—$R^{30}$ or —C(O)—$NR^{32}R^{31}$ radical;

wherein each $R^{30}$ is independently (1) alkyl, alkenyl or alkynyl radical optionally substituted by 1–3 radicals of —$CO_2R^{34}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, cyano, halo or aralkoxy, arylalkylthio, arylalkylsulfonyl, cycloalkyl, heterocyclyl, aryl or heteroaryl radicals, wherein the cycloalkyl, heterocyclyl, aryl and heteroaryl radicals are optionally substituted by 1–3 radicals of amino, alkylamino, dialkylamino, alkanoylamino, alkoxycarbonyl amino, alkylsulfonylamino, alkanoyl, alkoxycarbonyl, hydroxy, alkoxy, alkylthio, alkylsulfinyl, alkylsulfonyl, cyano, halo, alkyl, haloalkyl or haloalkoxy; (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl, haloalkyl or haloalkoxy; or (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl, haloalkyl or haloalkoxy;

preferably, each $R^{30}$ is independently (1) $C_1$–$C_8$ alkyl, $C_2$–$C_8$ alkenyl or $C_2$–$C_8$ alkynyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{30}$ is independently (1) $C_1$–$C_6$ alkyl radical optionally substituted by 1–3 radicals of —$CO_2R^{34}$, amino, $C_1$–$C_4$ alkylamino, di-($C_1$–$C_4$ alkyl) amino, $C_1$–$C_5$ alkanoylamino, ($C_1$–$C_4$ alkoxy) carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)-amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{30}$ is independently (1) $C_1$–$C_6$ alkyl radical optionally substituted by 1–3 radicals of —$CO_2R^{34}$, amino, $C_1$–$C_4$ alkylamino, di-($C_1$–$C_4$ alkyl) amino, $C_1$–$C_5$ alkanoylamino, ($C_1$–$C_4$ alkoxy) carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, —$CF_3$ or —$OCF_3$ radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_2$ haloalkyl of 1–3 halo radicals or —$OCF_3$; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio; cyano, halo, $C_1$–$C_4$ alkyl, —$CF_3$ or —$OCF_3$ radicals;

more preferably, each $R^{30}$ is independently (1) —$CF_3$ or $C_1$–$C_4$ alkyl radical optionally substituted by 1–2 radicals of —$CO_2R^{34}$, amino, $C_1$–$C_2$ alkylamino, di-($C_1$–$C_2$ alkyl)amino, $C_1$–$C_2$ alkanoylamino, ($C_1$–$C_4$ alkoxy)-carbonylamino, N—(($C_1$–$C_4$ alkoxy) carbonyl)-N—($C_1$–$C_4$-alkyl)amino, hydroxy, $C_1$–$C_4$ alkoxy, or aryl-$C_1$–$C_2$-alkoxy, heterocyclyl, aryl or heteroaryl radicals, wherein the heterocyclyl, aryl and heteroaryl radicals are optionally substituted by 1–3 radicals of amino, $C_1$–$C_2$ alkylamino, di-($C_1$–$C_2$ alkyl) amino, $C_1$–$C_2$ alkanoylamino, ($C_1$–$C_4$ alkoxy) carbonylamino, $C_1$–$C_5$ alkanoyl, ($C_1$–$C_4$ alkoxy) carbonyl, hydroxy, $C_1$–$C_4$ alkoxy, halo, $C_1$–$C_4$ alkyl, —$CF_3$ or —$OCF_3$ radicals; (2) heterocyclyl radical optionally substituted by 1–2 radicals of ($C_1$–$C_4$ alkoxy) carbonyl, hydroxy or $C_1$–$C_4$ alkyl; or (3) aryl or heteroaryl radicals optionally substituted by 1–2 radicals of amino, $C_1$–$C_2$ alkylamino, di-($C_1$–$C_2$ alkyl) amino, $C_1$–$C_2$ alkanoylamino, hydroxy, $C_1$–$C_2$ alkoxy, halo, $C_1$–$C_4$ alkyl, —$CF_3$ or —$OCF_3$ radicals;

more preferably, each $R^{30}$ is independently (1) heterocyclyl radical optionally substituted by 1–2 radicals of ($C_1$–$C_4$ alkoxy)carbonyl, hydroxy or $C_1$–$C_4$ alkyl; or (2) heteroaryl radicals optionally substituted by 1–2 radicals of amino, $C_1$–$C_2$ alkylamino, di-($C_1$–$C_2$ alkyl) amino, $C_1$–$C_2$ alkanoylamino, hydroxy, $C_1$–$C_2$ alkoxy, halo, $C_1$–$C_4$ alkyl, —$CF_3$ or —$OCF_3$ radicals; and most preferably, each $R^{30}$ is independently a heterocyclyl radical optionally substituted by $C_1$–$C_4$ alkyl;

wherein each $R^{31}$ is independently hydrogen radical or (1) alkyl, alkenyl or alkynyl radical optionally substituted by 1–3 radicals of —$CO_2R^{34}$, amino, alkylamino, dialkylamino, alkanoylamino, alkoxycarbonylamino; N-(alkoxycarbonyl)-N-(alkyl)amino, aminocarbonylamino, alkylsulfonylamino, hydroxy, alkoxy, alkylthio, alkylsulfinyl, alkylsulfonyl, cyano, halo or aralkoxy, arylalkylthio, arylalkylsulfonyl, cycloalkyl, heterocyclyl, aryl or heteroaryl radicals, wherein the cycloalkyl, heterocyclyl, aryl and heteroaryl radicals are optionally substituted by 1–3 radicals of amino, alkylamino, dialkylamino, alkanoylamino, alkoxycarbonylamino, alkylsulfonylamino, alkanoyl, alkoxycarbonyl, hydroxy, alkoxy, alkylthio, alkylsulfinyl, alkylsulfonyl, cyano, halo, alkyl, haloalkyl or haloalkoxy; (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl, haloalkyl or haloalkoxy; or (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl, haloalkyl or haloalkoxy;

preferably, each $R^{31}$ is independently hydrogen radical or (1) $C_1$–$C_8$ alkyl, $C_2$–$C_8$ alkenyl or $C_2$–$C_8$ alkynyl radical optionally substituted by 1–3 radicals of —$CO_2R^{34}$, amino, $C_1$–$C_4$ alkylamino, di-($C_1$–$C_4$ alkyl) amino, $C_1$–$C_5$ alkanoylamino, ($C_1$–$C_4$ alkoxy) carbonylamino, N—(($C_1$–$C_4$ alkoxy) carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{31}$ is independently hydrogen radical or (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{31}$ is independently hydrogen radical or (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, —$CF_3$ or —$OCF_3$ radicals; (2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_2$ haloalkyl of 1–3 halo radicals or —$OCF_3$; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

more preferably, $R^{31}$ is independently hydrogen radical or (1) —$CF_3$ or $C_1$–$C_4$ alkyl radical optionally substituted by 1–2 radicals of hydroxy, $C_1$–$C_2$ alkoxy or aryl-$C_1$–$C_2$-alkoxy, aryl or heteroaryl radicals, wherein the aryl and heteroaryl radicals are optionally substituted by 1–2 radicals of amino, $C_1$–$C_2$ alkylamino, di-($C_1$–$C_2$ alkyl) amino, $C_1$–$C_2$ alkanoylamino, ($C_1$–$C_4$ alkoxy)carbonylamino, $C_1$–$C_5$ alkanoyl, ($C_1$–$C_4$ alkoxy)carbonyl, hydroxy, $C_1$–$C_4$ alkoxy, halo, $C_1$–$C_4$ alkyl, —$CF_3$ or —$OCF_3$ radicals; or (2) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —$CF_3$ or —$OCF_3$ radicals; and most preferably, each $R^{31}$ is independently hydrogen radical or (1) —$CF_3$ or $C_1$–$C_4$ alkyl radical optionally substituted by 1–2 radicals of aryl or heteroaryl radicals; or (2) aryl or heteroaryl radical;

wherein each $R^{32}$ is independently (1) hydrogen radical; (2) alkyl, alkenyl or alkynyl radical optionally substituted by 1–3 radicals of amino, alkylamino, dialkylamino, hydroxy, alkoxy, alkylthio, cyano or halo; or (3) aryl, heteroaryl, arylalkyl, heteroarylalkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, cyano, alkyl, haloalkyl or haloalkoxy;

preferably, each $R^{32}$ is independently (1) hydrogen radical; (2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{32}$ is independently hydrogen or $C_1$–$C_4$ alkyl radical; and most preferably, each $R^{32}$ is independently a hydrogen or methyl radical;

wherein each $R^{33}$ is independently (1) hydrogen radical; (2) alkyl radical optionally substituted by a radical of heterocyclyl, aryl or heteroaryl which is optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy; or (3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy;

preferably, each $R^{33}$ is independently (1) hydrogen radical; (2) $C_1$–$C_4$ alkyl radical optionally substituted by a radical of heterocyclyl, aryl or heteroaryl which is optionally substituted by 1–3 radicals of amino, $C_1$–$C_4$ alkylamino, di-($C_1$–$C_4$ alkyl)amino, $C_1$–$C_5$ alkanoyl amino, ($C_1$–$C_4$ alkoxy)carbonylamino, $C_1$–$C_4$ alkylsulfonyl amino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; or (3) heterocyclyl, aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{33}$ is independently hydrogen or $C_1$–$C_4$ alkyl radical; and most preferably, each $R^{33}$ is independently a hydrogen or methyl radical; and wherein each $R^{34}$ is independently hydrogen, alkyl, aryl, heteroaryl, arylalkyl or heteroarylalkyl radical, wherein the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy;

preferably, each $R^{34}$ is independently hydrogen or $C_1$–$C_4$ alkyl, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;

more preferably, each $R^{34}$ is independently hydrogen or $C_1$–$C_4$ alkyl radical; and most preferably, each $R^{34}$ is independently a hydrogen or methyl radical.

The symbols used above have the following meanings:

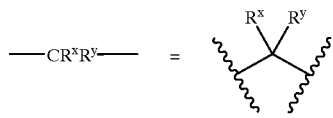

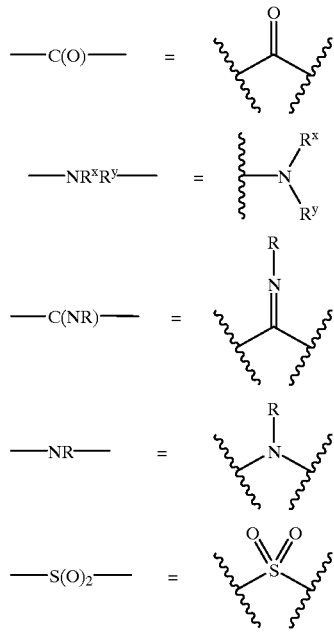

For example:

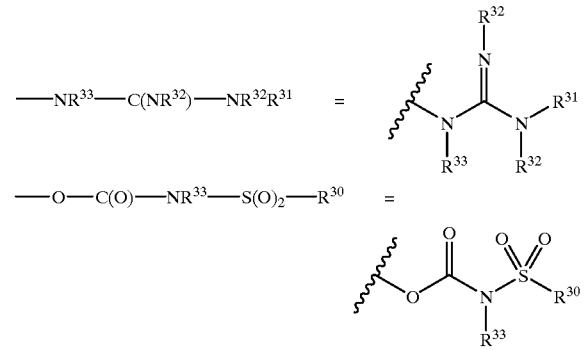

An aryl radical optionally substituted by an optionally substituted monocyclic heteroaryl or heterocyclyl radical of 5–6 ring members which is optionally substituted by a phenyl radical or monocyclic heteroaryl radical of 5–6 ring members means an aryl radical which is optionally substituted by (a) a monocyclic heteroaryl radical of 5–6 ring members optionally substituted by a phenyl radical or monocyclic heteroaryl radical of 5–6 ring members; or (b) a monocyclic heterocyclyl radical of 5–6 ring members optionally substituted by a phenyl radical or monocyclic heteroaryl radical of 5–6 ring members.

A heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members means a heteroaryl radical which is optionally substituted by (a) a phenyl radical optionally substituted by a phenyl radical or monocyclic heteroaryl radical of 5–6 ring members; (b) a monocyclic heteroaryl radical of 5–6 ring members optionally substituted by a phenyl radical or monocyclic heteroaryl radical of 5–6 ring members; or (c) a monocyclic heterocyclyl radical of 5–6 ring members optionally substituted by a phenyl radical or monocyclic heteroaryl radical of 5–6 ring members.

The compounds of this invention have in general several asymmetric centers and are depicted in the form of racemic mixtures. This invention is intended to encompass racemic mixtures, partially racemic mixtures and separate enantiomers and diasteromers. Preferably, the absolute configuration of the carboxylic acid group is (R). Preferably, the relative configuration of the carboxylic acid group and —NR$^{11}$R$^{33}$ is cis, i.e., the carboxylic acid and —NR$^{11}$R$^{33}$ are on the same face of the ring system.

Compounds of interest include the following:

3-amino-1-(4-methoxyphenylsulfonyl)azepane-2-carboxylic acid 3-(phenylmethylsulfonylamino)-1-(4-methoxyphenylsulfonyl)azepane-2-carboxylic acid 3-((2-aminophenyl)methylsulfonylamino)-1-(4-methoxyphenylsulfonyl)azepane-2-carboxylic acid cis-1-(4-Methoxy-benzenesulfonyl)-3-(phenylmethane sulfonylamino)-heptamethyleneimine-2-carboxylic acid trans-1-(4-Methoxy-benzenesulfonyl)-3-(phenylmethane sulfonylamino)-heptamethyleneimine-2-carboxylic acid 3-Benzyloxycarbonylamino-1-(4-methoxy-benzenesulfonyl)-1H-azepane-2-carboxylic acid 3-amino-1-(4-methoxyphenylsulfonyl)-2,3,4,7-tetrahydro-1H-azepine-2-carboxylic acid 3-(methylsulfonylamino)-1-(4-methoxyphenylsulfonyl)-2,3,4,7-tetrahydro-1H-azepine-2-carboxylic acid 3-(phenylsulfonylamino)-1-(4-methoxyphenylsulfonyl)-2,3,4,7-tetrahydro-1H-azepine-2-carboxylic acid 3-(naphth-2-ylsulfonylamino)-1-(4-methoxyphenylsulfonyl)-2,3,4,7-tetrahydro-1H-azepine-2-carboxylic acid 3-(naphth-1-ylsulfonylamino)-1-(4-methoxyphenylsulfonyl)-2,3,4,7-tetrahydro-1H-azepine-2-carboxylic acid 3-(phenylmethylsulfonylamino)-1-(4-methoxyphenylsulfonyl)-2,3,4,7-tetrahydro-1H-azepine-2-carboxylic acid 3-((2-nitrophenyl)methylsulfonylamino)-1-(4-methoxyphenylsulfonyl)-2,3,4,7-tetrahydro-1H-azepine-2-carboxylic acid 3-((2-phenylethenyl)sulfonylamino)-1-(4-methoxyphenylsulfonyl)-2,3,4,7-tetrahydro-1H-azepine-2-carboxylic acid 3-((4-iodophenyl)sulfonylamino)-1-(4-methoxyphenylsulfonyl)-2,3,4,7-tetrahydro-1H-azepine-2-carboxylic acid 3-(4-(4-chlorophenyl)phenyl)sulfonylamino)-1-(4-methoxyphenylsulfonyl)-2,3,4,7-tetrahydro-1H-azepine-2-carboxylic acid 3-(phenylmethoxycarbonylamino)-1-(4-methoxyphenylsulfonyl)-2,3,4,7-tetrahydro-1H-azepine-2-carboxylic acid 3-((4-trifluoromethylphenyl)methoxycarbonylamino)-1-(4-methoxyphenylsulfonyl)-2,3,4,7-tetrahydro-1H-azepine-2-carboxylic acid 3-((4-chlorophenyl)methoxycarbonylamino)-1-(4-methoxyphenylsulfonyl)-2,3,4,7-tetrahydro-1H-azepine-2-carboxylic acid 3-((3,5-dichlorophenyl)methoxycarbonylamino)-1-(4-methoxyphenylsulfonyl)-2,3,4,7-tetrahydro-1H-azepine-2-carboxylic acid 1-(4-Methoxy-benzenesulfonyl)-3-(4-Chlorophenyl-phenylsulfonylamino)-2,3,4,7-tetrahydro-1H-azepine-2-carboxylic acid 1-(4-Methoxy-benzenesulfonyl)-3-(4-chlorophenyl-methanesulfonylamino)-2,3,4,7-tetrahydro-1H-azepine-2-carboxylic acid 1-(4-Methoxy-benzenesulfonyl)-3(R)-(phenylmethane sulfonylamino)-heptamethyleneimine-2(S)-carboxylic acid trans-1-(4-Methoxy-benzenesulfonyl)-3(R)-(phenylmethanesulfonylamino)-heptamethyleneimine-2(R)-carboxylic acid.

As utilized herein, the following terms shall have the following meanings:

"Alkyl", alone or in combination, means a straight-chain or branched-chain alkyl radical containing preferably 1–15 carbon atoms ($C_1$–$C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkynyl", alone or in combination, means a straight-chain or branched chain hydrocarbon radical having one or more triple bonds, preferably 1–2 triple bonds and more preferably one triple bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkynyl radicals include ethynyl, propynyl (propargyl), butynyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like. "Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "R—S(O)$_2$" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Alkylsulfonylamino", alone or in combination, means a radical of the type "R—S(O)$_2$—NH—" wherein "R—S(O)$_2$—" is an alkylsulfonyl radical as defined above, wherein the amino radical may optionally be substituted, such as with alkyl, aryl, aralkyl, cycloalkyl, cycloalkylalkyl and the like.

"Aryl", alone or in combination, means a phenyl, biphenyl or naphthyl radical which is optionally substituted with one or more substituents selected from alkyl, alkoxy, halogen, hydroxy, amino, azido, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-CF$_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 4-(4-methoxyphenyl)phenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like. "Aryl-alkyl", alone or in combination, means an alkyl radical as defined above in which at least one hydrogen atom, preferably 1–2, is replaced by an aryl radical as defined above, such as benzyl, 1-2-phenylethyl, dibenzylmethyl, hydroxyphenylmethyl, methylphenylmethyl, diphenylmethyl, dichlorophenylmethyl, 2-naphthylmethyl, 4-methoxyphenylmethyl and the like.

"Aryl-alkoxy", alone or in combination, means an alkoxy radical as defined above in which at least one hydrogen atom, preferably 1–2, is replaced by an aryl radical as defined above, such as benzyloxy, 1-2-phenylethoxy, dibenzylmethoxy, hydroxyphenylmethoxy, methylphenylmethoxy, dichlorophenylmethoxy, 4-methoxyphenylmethoxy and the like.

"Aryloxy", alone or in combination, means a radical of the type "R—O—" wherein "R" is an aryl radical as defined above.

"Aroyl", alone or in combination, means a radical of the type "R—C(O)—" wherein "R" is an aryl radical as defined above and "—C(O)—" is a carbonyl.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonylamino", alone or in combination, means an amino substituted carbonyl substituted on a second amino (ureido) radical, wherein each amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Benzo", alone or in combination, means the divalent radical C$_6$H$_4$=derived from benzene.

"Bicyclic" as used herein is intended to include both fused ring systems, such as naphthyl and β-carbolinyl, and substituted ring systems, such as biphenyl, phenylpyridyl, naphthyl and diphenylpiperazinyl.

"Cycloalkyl", alone or in combination, means a saturated or partially saturated, preferably one double bond, monocyclic, bicyclic or tricyclic alkyl radical, preferably monocyclic, containing preferably 3–10 carbon atoms (C$_3$–C$_{10}$), more preferably 3–8 carbon atoms (C$_3$–C$_8$), even more preferably 3–6 carbon atoms (C$_3$–C$_6$), which is optionally be benzo fused and which is optionally substituted as defined herein with respect to the definition of aryl. Examples of such cycloalkyl radicals include cyclopropyl, cyclobutyl, cyclopentyl, cyclohexyl, dihydroxycyclohexyl, cycloheptyl, octahydronaphthyl, tetrahydronaphthyl, dimethoxytetrahydronaphthyl, 2,3-dihydro-1H-indenyl and the like.

"Cycloalkylalkyl", alone or in combination, means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, hydroxycyclopentylpropyl, tetrahydronaphthylpropyl, cyclohexylbutyl and the like.

"Heteroatoms" means nitrogen, oxygen and sulfur heteroatoms.

"Heterocyclyl", alone or in combination, means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl, ethylenedioxyphenyl and the like.

"Heterocyclylalkyl", alone or in combination, means an alkyl radical as defined above in which at least one hydrogen atom, preferably 1–2, is replaced by a heterocyclyl radical as defined above, such as pyrrolidinylmethyl, tetrahydrothienylmethyl, piperidinylethyl and the like.

"Heteroaryl", alone or in combination, means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally benzo fused or saturated carbocyclic fused, preferably 3–4 carbon atoms ($C_3$–$C_4$) to form 5–6 ring membered rings and which is optionally substituted as defined above with respect to the definitions of aryl and heterocyclyl. More preferably, "heteroaryl", alone or in combination, is a radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused. Examples of such heteroaryl groups include imidazolyl, 1-benzyloxycarbonylimidazol-4-yl, pyrrolyl, pyrazolyl, pyridyl, 2-(1-piperidinyl)pyridyl, 2-(4-benzyl piperazin-l-yl)-1-pyridinyl, pyrazinyl, triazolyl, furyl, thienyl, oxazolyl, thiazolyl, indolyl, quinolinyl, 1-oxido-2-quinolinyl, isoquinolinyl, 5,6,7,8-tetrahydroquinolyl, 5,6,7, 8-tetrahydroisoquinolinyl, quinoxalinyl, benzothiazolyl, 9-carbolinyl, benzofuryl, benzimidazolyl, benzoxazolyl and the like.

"Heteroaroyl", alone or in combination, means a radical of the type "R—C(O)—" wherein "R" is an heteroaryl radical as defined above and "—C(O)—" is a carbonyl.

"Heteroaryl-alkyl", alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl)methyl and the like.

"Haloalkoxy", alone or in combination, means an alkoxy radical as defined above in which at least one hydrogen atom, preferably 1–3, is replaced by a halogen radical, more preferably fluoro or chloro radicals. Examples of such haloalkoxy radicals include 2,2,2-trifluoroethoxy, chloromethoxy, 2-bromoethoxy, fluoromethoxy, difluoromethoxy, trifluoromethoxy, bis(trifluoromethyl)methoxy and the like.

"Sulfinyl", alone or in combination, means a diradical of the type "—S(O)—" wherein "S(O)" is a mono-oxygenated sulfur atom. "Sulfonyl", alone or in combination, means a diradical of the type "—S(O)$_2$—" wherein "S(O)$_2$" is a di-oxygenated sulfur atom.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

Procedures for preparing the compounds of this invention are set forth below. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Preparation of Compounds of Formula I

The compounds of the present invention represented by Formula I above can be prepared using various synthesis techniques, many of which are included by reference. In particular, compounds of the present invention can be prepared following the general procedures discussed below.

A general synthesis useful for the preparation of the novel compounds of this invention is illustrated in Scheme I, which employs a convergent route to the azepine ring and larger ring systems. According to this method, the readily available Horner-Emmons reagent is reacted under standard conditions (see Wadsworth, Org. Reactions, 1977, 25, 73) with an aldehyde variably substituted by a silyl ether as well as additional substitution on the alkyl chain (R5, R6, R9, R10) to provide the α,β unsaturated ester. Deprotection of the silyl group, activation of the alcohol to provide a leaving group and intramolecular base catalyzed closure provides a key intermediate. Subsequent deprotection of the t-BOC group with dry HCl/Ethyl acetate (Gibson, J. Org. Chem., 1994, 59, 3216) or with TFA and

SCHEME I

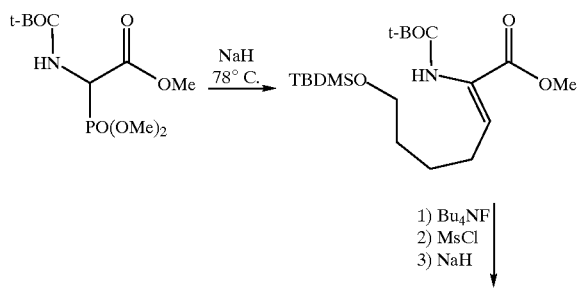

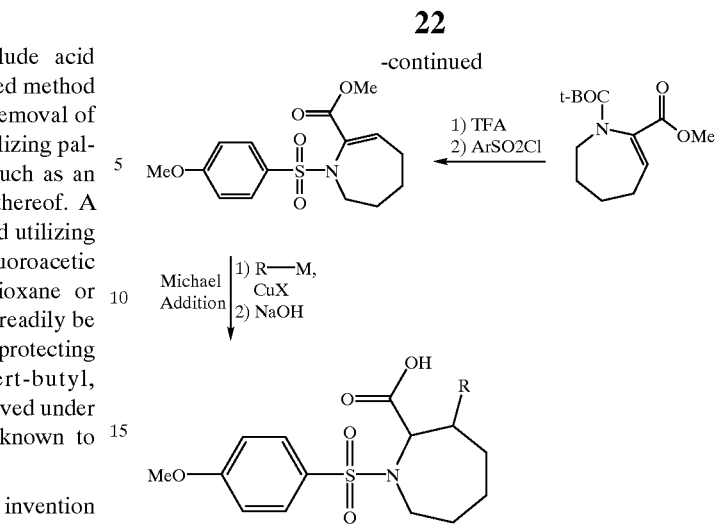

sulfonylation with a sulfonyl halide in the presence of a base, preferably a hindered amine base such as triethyl amine in a chlorinated solvent provides the substituted sulfonamide. The R group is a group that can be converted into an amino group using methods well known to those skilled in the art, such as benzyl amine, silyl protected benzyl amine, phthalimide, or other readily available nucleophilic amine equivalents. The protected primary amine is deprotected to the unsubstituted primary amine by methods known in the art for example hydrogenation in the presence of a metal catalyst. The primary amine is then funtionalized to provide the ester derivatives of the final product. Methods for funtionalization include sulfonylation as described above, treatment with isocyanates to prepare ureas, treatment with acid chlorides or mixed anhydrides to provide amides, reductive aminations to provide amines, and chloroformates to provide carbamates (See Compendium of Synthetic Organic Methods, Wiley). These adducts are treated with aqueous alkali bases such as LiOH to provide the free acid products when methyl or ethyl esters are used or TFA when the t-butyl ester is used as the ester component.

A second general synthesis useful for the preparation of the novel compounds of this invention is illustrated in Scheme II, which employs a convergent route to the azepine ring.

The readily available aspartic, or glutamic acid derivative is protected and allylated as described previously for an analog (see Baldwin, Tetrahedron, 1989, 45, 6309 and references cited therein). Mitsunobu reaction of the resulting sulfonamide (see Mitsunobu, Synthesis, 1981, 1) provides the bis olefin. Treatment of the resulting olefin with a metathesis reagent (see Schuster, Angew. Chem. Int. Ed. Engl. 1997, 36, 2036) provides the cyclized olefin. Saponification, as known by one skilled in the art, followed by curtius rearrangment of the resultant acid under known conditions (Tetrahedron, 1974, 30, 2151) provides the desired carbamates. The t-butyl acid protected carbamates can be deprotected with concentrated trifluoroacetic acid (TFA) to provide the final products. Additionally, by choosing the appropriate alcohol trapping agent for the Curtius rearrangement, for example, 4-methoxy benzyl alcohol, the carbamate may be diferentially deprotected to the amine with dilute (3%) TFA in a chlorinated solvent to provide the t-butyl protected acid, amine salt. Sulfonylation, as described previously, or treatment with the appropiate alkylating or acylating agent as known by one skilled in the art and deprotection of the t-butyl ester as described provides the compounds. Larger rings can be formed by using homologues of allyl-iodide or hydroxy-allyl, such as 4-iodo-1-butene, 4-hydroxy-1-butene, 5-iodo-1-pentene, 5-hydroxy-1-pentene, 4-iodo-2-butene, 4-hydroxy-2-butene and the like.

undergo allylic oxidation with chromium or preferably selenium reagents (see Rabjohn, Org. Reactions, 1976, 24, 261) as known in the art to provide allylic alcohols which activated as a leaving group and can be substituted with

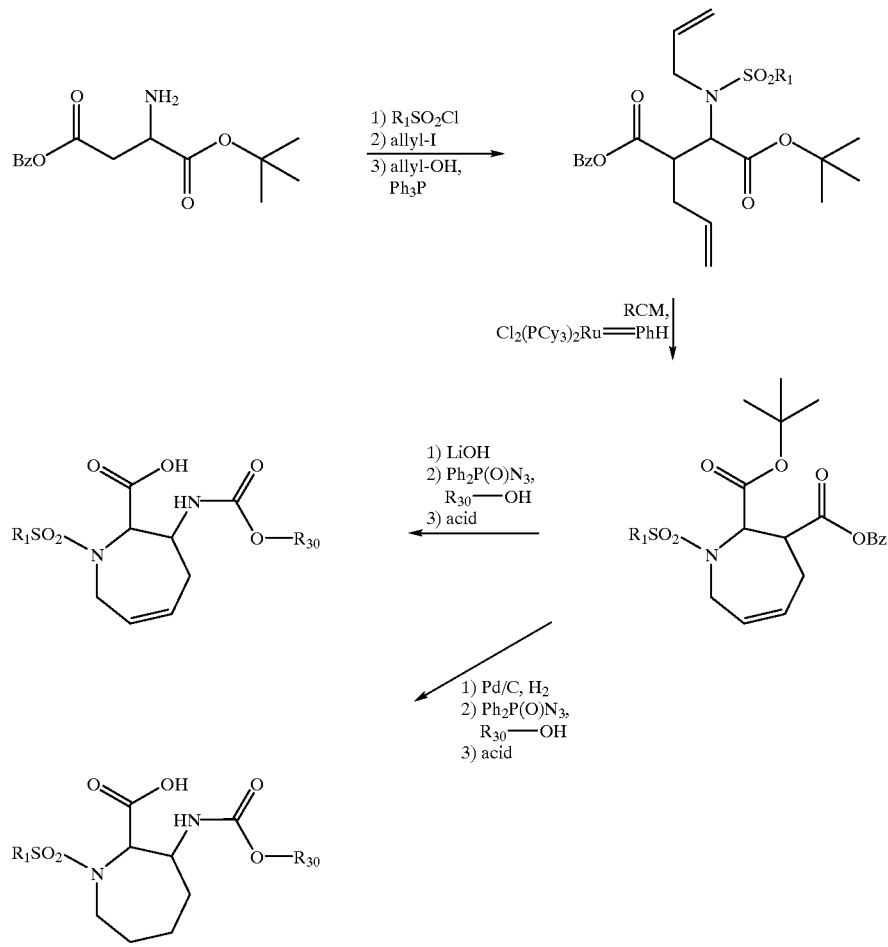

SCHEME II

Intermediates from Scheme II can be used as starting materials for substituents $R^5$, $R^6$, $R^9$ and $R^{10}$. For example, the aspartic acid derivative can be alkylated with a variety of polysubstiuted allyl iodides or triflates such as $CH_2=CH_2CHR^7R^{10}I$ followed by Mitzunubu reaction with with allyl and homoallyl alcohols to provide intermediates for methathesis reaction. The compounds claimed may also be prepared by funtionalization of the olefinic intermediates after metathesis. For example, the olefin can be hydrogenated under standard conditions, preferably, Pd/C under an atmosphere of hydrogen in a solvent such as a alcohol,or ethyl acetate. The olefin can be hydroborated with a borane reagent,(see Brown, Borane Reagents, Academic Press, NY, 1988) preferably, $BH_3$-DMS, and the subsequent borane complex oxidized with $H_2O_2$ to provide the alcohol or with cromium agents under standard conditions (see Hudlicky, Oxidations in Organic Chemistry, ACS mongraph 186, 1990), provides the ketone. The ketone can serve as a electrophil with wittig reagents, organometallic agents or can be reacted with aldehydes under basic or acidic conditions to undergo aldol condensations. The olefins can carbon, oxygen, nitrogen or sulphur nucleophiles as known in the art under neutral or basic conditions with or without palladium or lewis acid catalysis. Additional compounds can be prepared by treatment of the olefin with a aryl or alkenyl halide or triflate in the presence of a palladium catalyst to undergo a Heck reaction. (for an extensive review of bond formation using palladium catalysis see Tsuji, Palladium Reagents and Catalysis, Wiley, 1995) The formed olefin can be funtionalized as described above to provide additional substitution. The olefin can be epoxidized with MCPBA or a related peroxide to for the epoxide that can be substituted in the presence or absence or a lewis acid with a reactive Carbon, nitrogen, oxygen or sulphur nucleophil as known in the art.

Alternatively, substituted urea derivatives can be prepared by reacting the isocyanate intermediate formed in the Curtius rearrangement by using an amine ($HNR^{31}R^{32}$) in place of the alcohol ($R^{30}$—OH) (Scheme III).

SCHEME III

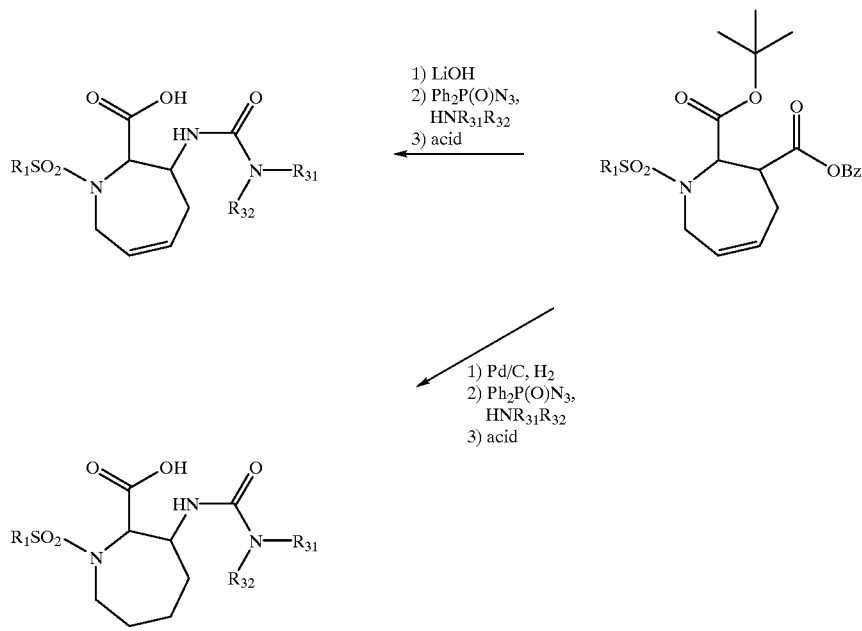

SCHEME IV

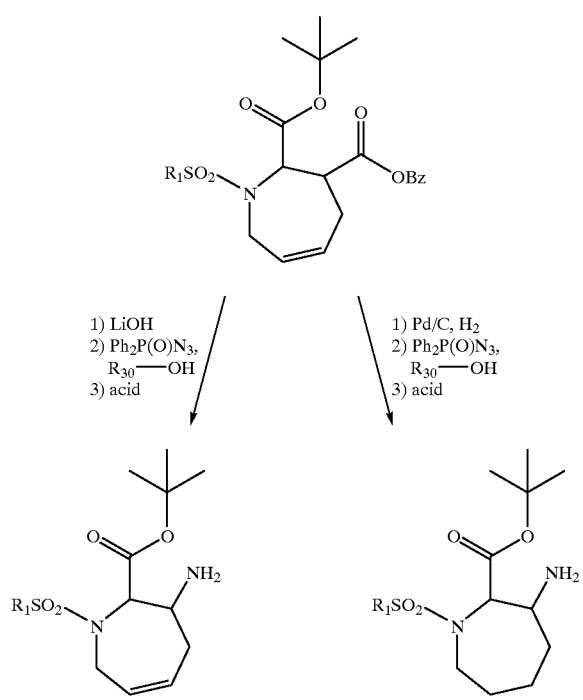

Further, the carbamate formed in Scheme II can be hydrolyzed in acid to the free amine (Scheme IV) which can then be derivatized, such as by alkylation, reductive alkylation, sulfonylation, aminosulfonylation, acylated and the like, such as in Scheme V.

SCHEME V

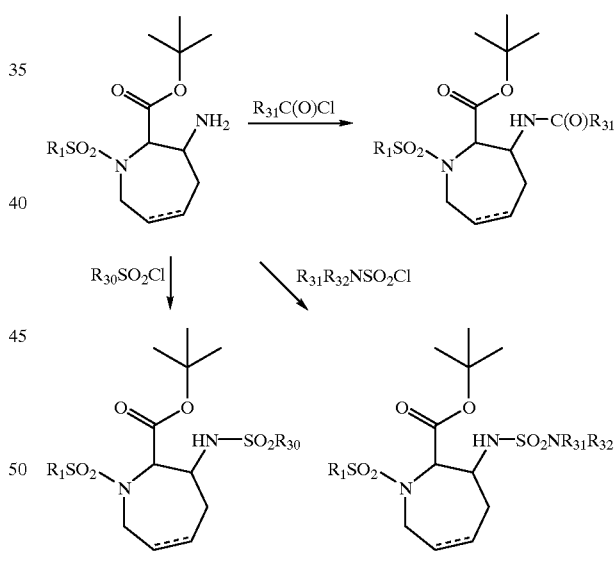

It is apparent from the above description that no single general synthesis can be used in the preparation of all of the novel compounds of this invention, because some of the radicals, well known to those skilled in the art, will or may have the potential of interfering with, competing with or inhibiting the some of the reactions involved in the pathway. However, one skilled in the art is fully aware of appropriate point in the synthetic pathway when a radical may be introduced and when protecting groups can be used.

Sulfonyl halides can be prepared by the reaction of a suitable alkyl, aryl, heteroaryl, heterocyclyl and the like Grignard or lithium reagents with sulfuryl chloride, or sulfur dioxide followed by oxidation with a halogen, preferably chlorine. Alkyl, heteroaryl, heterocyclyl, aryl and the like Grignard or lithium reagents can be prepared from their corresponding halide (such as chloro or bromo) compounds which are commercially available or readily prepared from commercially available starting materials using known methods in the art. Alternatively, mercaptans may be oxidized to sulfonyl chlorides using chlorine in the presence of water under carefully controlled conditions. Additionally, sulfonic acids may be converted into sulfonyl halides using reagents such as $PCl_5$, $SOCl_2$, $ClC(O)C(O)Cl$ and the like, and also to anhydrides using suitable dehydrating reagents. The sulfonic acids are either commercially available or may be prepared using procedures well known in the art from commercially available starting materials. In place of the sulfonyl halides, sulfinyl halides or sulfenyl halides can be utilized to prepare compounds wherein the sulfonyl moiety is replaced by an sulfinyl or thio moiety, respectively. Arylsulfonic acids, benzo fused heterocyclyl sulfonic acids or heteroaryl sulfonic acids can be prepared by sulfonation of the aromatic ring by well known methods in the art, such as by reaction with sulfuric acid, $SO_3$, $SO_3$ complexes, such as $DMF(SO_3)$, $pyridine(SO_3)$, N,N-dimethylacetamide $(SO_3)$, and the like. Preferably, such sulfonyl halides are prepared from such aromatic compounds by reaction with DMF $(SO_3)$ and $SOCl_2$ or $ClC(O)C(O)Cl$. The reactions may be performed stepwise or in a single pot.

Additional R1 substitution can be obtained by further reactions on the sulfonamide after reaction of the sulfonyl halide with the related amine. For instance, nitro substituted aryl or heteroaryl sulphonamides can be reduced to the aniline and substituted or converted to the diazonium salt and reacted further to provide the described compounds by methods known to one skilled in the art. Additional R1 substitutions can be obtained by reaction of fluorine, halogen, or trifluoromethanesulfonyloxy substituted aryl or heteroaryl or alkyl sulfonyl chlorides with the related amine followed by substitution of the reactive intermediate with oxygen, nitrogen, sulfur or carbon nucleophile in the presence or absence of a transition metal catalyst such as palladium to provide the desired compounds. (For a monograph on the topic, see Miller, Aromatic Nucleophilic Substitution, Elsevier, NY, 1968).

Alkyl sulfonic acids, aryl sulfonic acids, heterocyclyl sulfonic acids, heteroaryl sulfonic acids, alkylmercaptans, arylmercaptans, heterocyclylmercaptans, heteroarylmercaptans, alkylhalides, arylhalides, heterocyclylhalides, heteroarylhalides, and the like are commercially available or can be readily prepared from starting materials commercially available using standard methods well known in the art.

Thioether derivatives can be converted into the corresponding sulfone or sulfoxide by oxidizing the thioether derivative with a suitable oxidation agent in a suitable solvent. Suitable oxidation agents include, for example, hydrogen peroxide, sodium meta-perborate, oxone (potassium peroxy monosulfate), meta-chloroperoxy benzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The compounds of the invention may be produced in racemic or optically pure form. When a single enantiomer is prepared, these may be synthesized by beginning with optically pure starting materials, by resolution of a basic or acidic racemic intermediate with the appropriate chiral acid or base respectivily, as known to one skilled in the art, or by the addition of a chiral protecting group to the racemic intermediate or final product where the diasteriomeric pair can be seperated by chromatoraphy or crystallization.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Prodrugs of the compounds of this invention are also contemplated by this invention. A prodrug is an active or inactive compound that is modified chemically through in vivo physiological action, such as hydrolysis, metabolism and the like, into a compound of this invention following adminstration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on a Bruker nuclear magnetic resonance spectrometer.

The following Examples illustrate the preparation of compounds of the present invention and intermediates useful in preparing the compounds of the present invention.

EXAMPLE 1

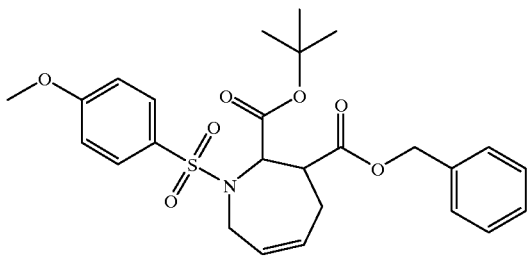

Preparation of 1-(4-Methoxy-benzenesulfonyl)-2,3, 4,7-tetrahydro-1H-azepine-2,3-dicarboxylic acid 3-benzyl ester 2-tert-butyl ester Step A. 2-Aminosuccinic Acid 4-benzyl Ester 1-tert-butyl ester D-Aspartic acid β-benzylester (9 g, 40.3 mmol) is suspended in 75 ml Dioxane and 7.5 ml Sulfuric Acid and cooled to −15° C. 2-Methylpropene (75 ml) is added and the reaction mixture is sealed and stirred for 4 h at room temperature. The reaction mixture is then cooled to 0° C. and poured into 600 ml Diethylether and 325 ml 1M NaOH. The organic phase is separated and the water phase is extracted twice with 200 ml Diethylether. The combined organic fractions are dried with $MgSO_4$ for 30 min. and filtered. The Diethylether is evaporated and the remaining oil is dried at high vacuum for 24 hours:

Cal. 280.2, found $(M)^+280$.

Step B. 2-(4-Methoxy-benzenesulfonylamino)-succinic acid 4-benzyl ester 1-tert-butyl ester 2-Aminosuccinic acid 4-benzyl ester 1-tert-butyl ester (9.57 g, 33.4 mmol), Triethylamine (9.3 ml, 66.8 mmol) and 4-Methoxybenzenesulfonylchloride (6.9 g, 33.4 mmol) are solved in 50 ml Dichloromethane (DC) and stirred at room temp. for 1 h. The reaction mixture is diluted with 50 ml DCM. 200 ml water are added and the organic phase is separated. The water phase is extracted twice with DCM. The combined organic extracts are dried with $MgSO_4$ and filtered. The solvent is evaporated and the remaining residue is recrystallized from Diethylether/Ethylacetate as white needles: $^1H$ NMR ($CDCl_3$), ppm: 8.2 Hz, (d, 1H), 7.7 Hz (d, 2H), 7.3 Hz (m, 5H), 7.1 Hz (d, 2H), 5.05 Hz (d, 2H), 4.08 Hz (dd, 1H), 3.9 Hz (s, 3H), 2.72 Hz (dd, 1H), 2.59 Hz (dd, 1H) 1.21 Hz (s, 9H).

Step C. 2-Allyl-3-(4-methoxy-benzenesulfonylamino)-succinic acid 1-benzyl ester 4-tert-butyl ester 100 ml dry Tetrahydrofuran (THF) are cooled to −78° C. 1M THF-solution of Lithium bis(trimethylsilyl)amide (47.35 ml, 47.35 mmol) are added while the temperature is maintained. 2-(4-Methoxy-benzenesulfonylamino)-succinic acid 4-benzyl ester 1-tert-butyl ester (10.1 g, 22.5 mmol) are dissolved in 45 ml THF and added dropwise to the reaction solution. The reaction mixture is allowed to stir for 1h and then warmed briefly to −40° C. After re-cooling to −78° C. Allyliodide (3.1 ml, 33.8 mmol) dissolved in 30 ml THF are added drop-wise. The reaction mixture is allowed to warm to −40° C. and is quenched with a $NH_4Cl$-solution. The organic phase is separated dried over $MgSO_4$ and filtered. The solvent is evaporated and the product is purified with a short flash-chromatography column. Hexane/Ethylacetate (9:1):

Cal. 489.6 Found. $(M)^+490$.

Step D. 2-Allyl-3-[allyl-(4-methoxy-benzenesulfonyl)-amino]-succinic Acid 1-benzyl ester 4-tert-butyl Ester Triphenylphosphine (1 g, 3.9 mmol) are solved in 60 ml Tetrahydrofuran (THF) and cooled to 0° C. Diazopropyl dicarboxylate (DIAD) (0.77 ml, 3.9 mmol) are added via syringe and the reaction mixture is stirred for 30 min. Allyl alcohol (16 μl, 0.23 mmol) is added to the yellow suspension and then after 10 min., 2-Allyl-3-(4-methoxy-benzenesulfonylamino)-succinic acid 1-benzyl ester 4-tert-butyl ester (1.4 g, 2.6 mmol) is added. The reaction mixture is stirred for 30 min. at 0° C. and is then allowed to warm to room temp. After evaporation of most of the THF and flash-chromatography with Hexane/Ethylacetate (2:1) the desired product is obtained: $^1H$ NMR ($CDCl_3$ 400 MHz), ppm: 7.80 (d, 2H), 7.38 (m, 5H), 6.95 (d, 2H), 5.75 (m, 2H), 5.10 (m, 6H), 3.95 (m, 2H), 3.90 (s, 3H), 3.21 (ddd, 1H), 2.50 (ddd, 1H), 2.35 (ddd, 1H), 1.40 (s, 9H).

Step E. 1-(4-Methoxy-benzenesulfonyl)-2,3,4,7-tetrahydro-1H-azepine-2,3-dicarboxylic acid 3-benzyl ester 2-tert-butyl ester 2-Allyl-3-[allyl-(4-methoxy-benzenesulfonyl)-amino]-succinic acid 1-benzyl ester 4-tert-butyl ester (5.5 g, 10.4 mmol) are solved in 40 ml Dichloromethane and deoxygenated and flushed with Argon three times. The catalyst $(RuCl_2(PCy_3)_2=\!\!=\!\!-Ph)$ (100 mg, 0.12 mmol) is added and the reaction is deoxygenated and flushed with Argon one more time. The reaction solution is stirred for 7 h at room temperature. Another (90 mg, 0.11 mmol) of the Ruthenium catalyst are added and the reaction is stirred over night. Evaporation of the solvent followed by flash-chromatography, Hexane/Ethylacetate (3:1) afforded the product: $^1H$ NMR ($CDCl_3$ 400 Mhz), ppm: 7.81 (d, 2H), 7.37 (m, 5H), 6.93 (d, 2H), 5.60 (m, 2H), 5.10 (m, 3H), 4.18 (dd, 1H), 4.05 (dd, 1H), 3.88 (s, 3H), 3.20 (ddd, 1H), 2.68 (m, 2H), 1.32 (s, 9H).

EXAMPLE 2

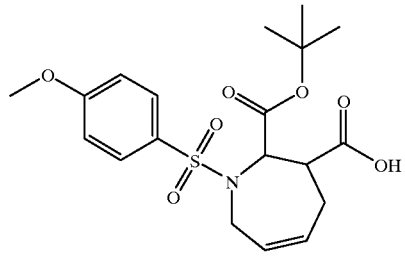

Preparation of 1-(4-Methoxy-benzenesulfonyl)-2,3, 4,7-tetrahydro-1H-azepine-2,3-dicarboxylic acid 2-tert-butyl ester 1-(4-Methoxy-benzenesulfonyl)-2,3,4,7-tetrahydro-1H-azepine-2,3-dicarboxylic acid 3-benzyl ester 2-tert-butyl ester (6 g, 12 mmol) is dissolved in a mixture of 120 ml Tetrahydrofuran and 78 ml Water. $LiOH·H_2O$ (1 g, 24 mmol) is added. After 45 min., more Water (15 ml) is added and the reaction solution is stirred at room temp. for 24 h. The solvent is evaporated and the remaining solid is resolved in Water/Diethylether. The water layer is acidified to pH 1. The organic phase is separated and the water phase is extracted twice with Ethylacetate. The combined organic fractions are dried with $MgSO_4$ and filtered. The solvent is evaporated to afford the product: Cal. 412.5, found $(M)^+$ 412.1.

EXAMPLE 3

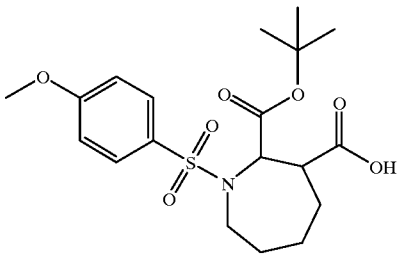

Preparation of 1-(4-Methoxy-benzenesulfonyl)-azepane-2,3-dicarboxylic acid 2-tert-butyl ester 1-(4-Methoxy-benzenesulfonyl)-2,3,4,7-tetrahydro-1H-azepine-2,3-dicarboxylic acid 3-benzyl ester 2-tert-butylester (2.28 g, 4.5 mmol) are dissolved in 40 ml Dioxane/Methanol (3:1). Palladium on charcoal (10%) (170 mg, 0.16 mmol) are added under an Argon flow. The flask is evacuated and flushed three times with Hydrogen. The reaction is stirred for 6 h at room temperature. Filtration through Celite and evaporation of the solvents afforded the product: $^1$H NMR (DMSO, 400 MHz), ppm: 7.81 (d, 2H), 6.95 (d, 2H), 5.40 (d, 1H), 3.68 (s, 3H), 3.65 (m, 1H), 3.25 (m, 1H), 2.92 (m, 1H), 2.15 (m, 1H), 1.95 (m, 1H), 1.78 (m, 2H) 1.25 (s, 9H).

EXAMPLE 4

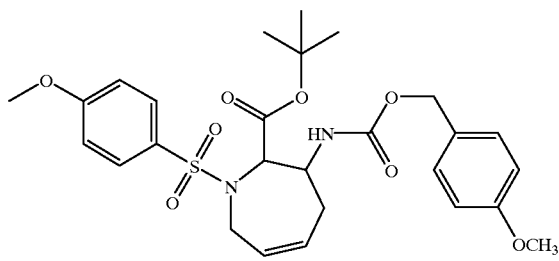

Preparation of 1-(4-Methoxy-benzenesulfonyl)-3-(4-methoxy-benzyloxycarbonyl-amino)-2,3,4,7-tetrahydro-1H-azepine-2-carboxylic acid tert-butyl ester The reaction is performed under an Argon atmosphere and exclusion of light. 1-(4-Methoxy-benzenesulfonyl)-2,3,4,7-tetrahydro-1H-azepine-2,3-dicarboxylic acid 2-tert-butyl ester (550 mg, 1.34 mmol) is dissolved in 7 ml dry Tetrahydrofuran (THF). Tripropyl amine (TPA) (280 µl, 1.47 mmol) is added and the reaction is stirred for 30 minutes at RT. Diphenyl phosphoryl azide (318 µl, 1.47 mmol) is added and the reaction is gradually heated to 40° C. for 3 h. The reaction temperature is then increased to reflux conditions for 6 h. The reaction mixture is allowed to cool to room temperature and 4-Methoxybenzylalcohol (184 µl, 1.47 mmol) is added. The, reaction is heated to reflux over night. The solvent is evaporated. Flash-chromatography Hexane/Ethylacetate (2:1) afforded the product: Cal. 383.5 found (M)$^+$ 383.0.

EXAMPLE 5

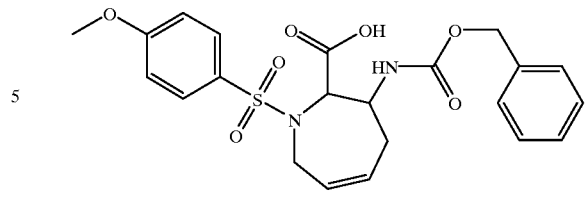

Preparation of 3-Benzyloxycarbonylamino-1-(4-methoxy-benzenesulfonyl)-2,3,4,7-tetrahydro-1H-azepine-2-carboxylic acid Step A. 3-Benzyloxycarbonylamino-1-(4-methoxy-benzenesulfonyl)-2,3,4,7-tetrahydro-1H-azepine-2-carboxylic acid tert-butyl ester The reaction is performed under an Argon athmosphere. 1-(4-Methoxy-benzenesulfonyl)-2,3,4,7-tetrahydro-1H-azepine-2,3-dicarboxylic acid 2-tert-butyl ester (300 mg, 0.73 mmol) is dissolved in 4 ml Dioxane (dry). Tripropylamine (TPA) (98 µl, 0.73 mmol) is added and the reaction is stirred for 15 minutes at RT. Diphenyl phosphoryl azide (157µl, 0.73 mmol) is added and the reaction is gradually heated to 60° C. for 3 h. The reaction is then allowed to cool to room temperature. Benzyl alcohol (235 µl, 2.2 mmol) is added and the reaction solution is heated to 60° C. over night. The reaction solution is diluted with Ethylacetate and washed with 2 M Citric Acid and Water. The organic phase is separated, dried with MgSO$_4$ and filtrated. The solvent is evaporated and the remaining oil is purified by flash-chromatography, Hexane/Ethylacetate (2:1):
Cal. 516.6, found (M)$^+$ 517.

Step B. 3-Benzyloxycarbonylamino-1-(4-methoxy-benzene sulfonyl)-2,3,4,7-tetrahydro-1H-azepine-2-carboxylic Acid 3-Benzyloxycarbonylamino-1-(4-methoxy-benzenesulfonyl)-2,3,4,7-tetrahydro-1H-azepine-2-carboxylic acid tert-butyl ester (28 mg, 0.054 mmol) is dissolved in 4 ml Dichloro-methane/Trifluoroacetic Acid; 3:1 and stirred for 5 h at room temperature. The solvent/reagent are evaporated and the remaining oil is co-evaporated from Toluene twice. Flash-chromatography, Hexane/Ethylacetate; 1:1 afforded the desired product: Cal. 460.51, found (M)$^+$ 460.9.

EXAMPLE 6

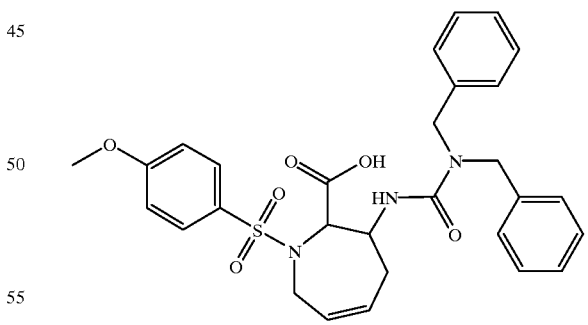

Preparation of 3-(3,3-Dibenzylureido)-1-(4-methoxy-benzenesulfonyl)-2,3,4,7-terahydro-1H-azepine-2-carboxylic acid Step A. 3-(3,3-Dibenzylureido)-1-(4-methoxy-benzenesulfonyl)-2,3,4,7-tetrahydro-1H-azepine-2-carboxylic acid tert-butyl ester The reaction is performed under an Argon blanket. 1-(4-Methoxy-benzenesulfonyl)-2,3,4,7-tetrahydro-1H-azepine-2,3-dicarboxylic acid 2-tert-butyl ester (204 mg, 0.5 mmol) is dissolved in 10 ml dry Dioxane. Tripropylamine (94 µl, 0.5 mmol) is added and then Diphenyl phosphoryl azide (DPPA). The reaction is heated to 75° C. for 5 h. After cooling to room temperature, Dibenzylamine (190.6 µl, 1 mmol) is added via syringe. The reaction is heated to 70° C. and stirred over night. Evaporation of the solvents and flash-chromatography, Hexane/Ethyl acetate (1:1) afforded the product: Cal. 606.8 found (M)+ 606.2.

Step B. 3-(3,3-Dibenzylureido)-1-(4-methoxy-benzene sulfonyl)-2,3,4,7-terahydro-1H-azepine-2-carboxylic acid 3-(3,3-Dibenzylureido)-1-(4-methoxy-benzenesulfonyl)-2,3,4,7-tetrahydro-1H-azepine-2-carboxylic acid tert-butyl ester (200 mg, 0.33 mMol) is reacted in the same manner as 3-Benzyloxycarbonylamino-1-(4-methoxy-benzenesulfonyl)-2,3,4,7-tetrahydro-1H-azepine-2-carboxylic acid tert-butyl ester and purified by flash-chromatography, Dichloromethane/Methanol (9:1) to afford the free acid: Cal. 550.6 found (M)+=550.

EXAMPLE 7

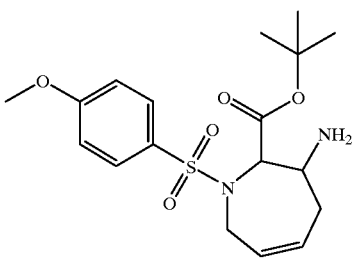

Preparation of 3-Amino-1-(4-methoxy-benzenesulfonyl)-2,3,4,7-tetrahydro-1H-azepine-2-carboxylic acid tert-butyl ester 1-(4-Methoxy-benzenesulfonyl)-3-(4-methoxybenzyloxy carbonyl-amino)-2,3,4,7-tetrahydro-1H-azepine-2-carboxylic acid tert-butyl ester (370 mg, 0.71 mMol) is dissolved in Dichloromethane (15 ml) containing 3% Trifluoroacetic Acid. The reaction is stirred for 1 h at room temperature. The solvents are evaporated and the remaining oil is co-evaporated twice with Toluene. Flash-chromatography Dichloromethane/Methanol (7:1) to afford the free amine: Cal. 546.6 found (M)+=547.

EXAMPLE 8

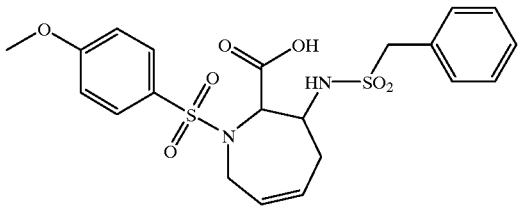

Preparation of 1-(4-Methoxy-benzenesulfonyl)-3-(phenylmethanesulfonylamino)-2,3,4,7-tetrahydro-1H-azepine-2-carboxylic acid Step A. 1-(4-Methoxy-benzenesulfonyl)-3-(phenylmethaneSulfonylamino)-2,3,4,7-tetrahydro-1H-azepine-2-carboxylic acid tert-butyl ester 3-Amino-1-1(4-methoxy-benzenesulfonyl)-2,3,4,7-tetrahydro-1H-azepine-2-carboxylic acid tert-butyl ester (38 mg, 0.1 mmol) is dissolved in 3 ml dry Dichloromethane. Hunigs Base (42 µl, 0.24 mmol) is added and then alpha-Toluenesulfonyl chloride (28.4 mg, 0.15 mmol) is added. The reaction mixture is stirred at room temperature for 4 h. The solvent is evaporated and the remaining oil is purified by Flash-chromatography Hexane/Ethylacetate (2:1): 1H NMR (CDCl3 400 MHz), ppm: 7.75 (d, 2H), 7.50 (m, 2H),7.4 (m, 3H) 6.99 (d, 2H), 5.70 (m, 2H), 4.85 (d, 1H), 4.56 (d, 1H), 4.35 (dd, 2H), 4.22 (dd, 1H), 4.02 (m, 1H), 3.90 (m, 3H), 3.83 (m, 1H),2.50 (m, 1H), 2.30 (m, 1H), 1.30 (s, 9H).

Step B. 1-(4-Methoxy-benzenesulfonyl)-3-(phenylmethane Sulfonylamino)-2,3,4,7-tetrahydro-1H-azepine-2-carboxylic acid 1-(4-Methoxy-benzenesulfonyl)-3-(phenylmethanesulfonyl amino)-2,3,4,7-tetrahydro-1H-azepine-2-carboxylic acid tert-butyl ester (29 mg, 0.054 mmol) is reacted in the same manner as 3-Benzyloxycarbonylamino-1-(4-methoxy-benzenesulfonyl)-2,3,4,7-tetrahydro-1H-azepine-2-carboxylic acid tert-butyl ester: Cal. 479.5 found (M–H)+ 478.6. Cal. 498.6, found (MNH4)+498.1; 1H NMR (DMSO, 400 MHz), ppm: 7.85 (d, 2H), 7.38 (m, 5H) 7.01 (d, 2H), 5.5 (m, 2H) 4.45 (d, 2H), 4.30 (d, 2H), 4.15 (m, 2H), 4.00 (m, 1H), 3.90 (dd, 1H), 3.83 (s, 3H), 2.18 (m, 2H).

EXAMPLE 9

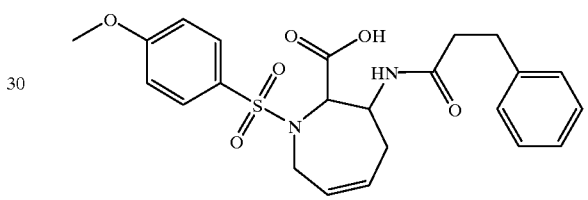

Preparation of 1-(4-Methoxy-benzenesilfonyl)-3-(3-phenylpropionylamino)-2,3,4,7-tetrahydro-1H-azepine-2-carboxylic Acid Step A. 1-(4-Methoxy-benzenesulfonyl)-3-(3-phenyl-propionylamino)-2,3,4,7-tetrahydro-1H-azepine-2-carboxylic acid tert-butyl ester 3-Amino-1-(4-methoxy-benzenesulfonyl)-2,3,4,7-tetrahydro-1H-azepine-2-carboxylic acid tert-butyl ester (31 mg, 0.08 mmol) is dissolved in 4 ml Dichloromethane and cooled to 0° C. Hunigs Base (34 µl, 0.2 mmol) is added followed by Hydrocinnamyl chloride (18 µl, 0.12 mmol). The reaction is stirred 1 h at 0° C. and is then allowed to warm to room temperature. The solvents are evaporated and the remaining oil is purified by flash-chromatography, Dichloro-methane/Methanol (9:1) affording the product: Cal. 513.6 found (M+H)+=514.9.

Step B. 1-(4-Methoxy-benzenesulfonyl)-3-(3-phenylpropionylamino)-2,3,4,7-tetrahydro-1H-azepine-2-carboxylic acid 1-(4-Methoxy-benzenesulfonyl)-3-(3-phenylpropionylamino)-2,3,4,7-tetrahydro-1H-azepine-2-carboxylic acid tert-butyl ester (22 mg, 0.04 mmol) is reacted in the same manner as 3-Benzyloxycarbonylamino-1-(4-methoxy-benzenesulfonyl)-2,3,4,7-tetrahydro-1H-azepine- 2-carboxylic acid tert-butyl ester and purified by flash-chromatography, Dichloromethane/Methanol (9:1) to afford the acid: Cal. 457.5 found (M–H)+ 456.6; 1H NMR (DMSO, 400 MHz), ppm: 7.78 (d, 2H), 7.28 (m, 2H), 7.20 (m, 3H), 7.01 (d, 2H), 5.6 (m, 1H), 5.5 (m, 1H), 4.3 (m, 3H), 4.0 (m, 1H), 3.82 (s, 3H), 2.8 (t, 2H), 2.35 (m, 2H), 2.05 (m, 2H).

EXAMPLE 10

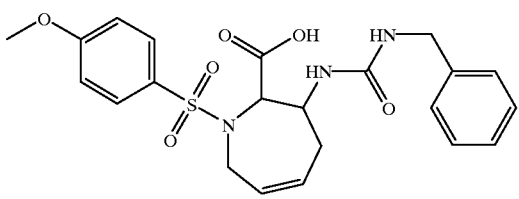

Preparation of 3-(3-Benzylureido)-1-(4-methoxy-benzenesulfonyl)-2,3,4,7-tetrahydro-1H-azepine-2-carboxylic acid Step A. 3-(3-Benzylureido)-1-(4-methoxy-benzenesulfonyl)-2,3,4,7-tetrahydro-1H-azepine-2-carboxylic acid tert-butyl ester 3-Amino-1-(4-methoxy-benzenesulfonyl)-2,3,4,7-tetrahydro-1H-azepine-2-carboxylic acid tert-butyl ester (33 mg, 0.09 mmol) is solved in 3 ml dry Dioxane. Benzylisocyanate (10.6 µl, 0.086 mmol) is added and the reaction is stirred at room temperature for 1 h. Evaporation of the solvent and flash-chromatography, Dichloromethane/Methanol (7:1) afforded the product:
Cal. 515.6 found (M)+ 515.9.

Step B. 3-(3-Benzylureido)-1-(4-methoxy-benzenesulfonyl)-2,3,4,7-tetrahydro-1H-azepine-2-carboxylic acid 3-(3-Benzylureido)-1-(4-methoxy-benzenesulfonyl)-2,3,4,7-tetrahydro-1H-azepine-2-carboxylic acid tert-butyl ester (25 mg, 0.05 mmol) is reacted in the same manner as 3-Benzyloxycarbonylamino-1-(4-methoxy-benzenesulfonyl)-2,3,4,7-tetrahydro-1H-azepine-2-carboxylic acid tert-butyl ester and purified by flash-chromatography, Dichloromethane/Methanol (9:1): Cal. 459.5 found (M–H)+ 458.2; $^1$H NMR (DMSO, 400 MHz), ppm: 7.79 (d, 2H), 7.30 (m, 2H),7.20 (m, 3H) 7.02 (d, 2H), 5.60 (m, 1H), 5.50 (m, 1H) 4.3 (m, 3H), 4.00 (m, 1H), 3.93 (m, 3H), 2.81 (t, 2H),2.35 (m, 2H), 2.05 (m, 2H).

EXAMPLE 11

Using the procedures of the above general descriptions and Examples 1–10 above, the following compounds were prepared:

1-(4-Methoxy-benzenesulfonyl)-3-(phenylethanesulfonylamino)-1H-azepane-2-carboxylic acid: Cal. 496.6 found (M)+ 497;

1-(4-Methoxy-benzenesulfonyl)-3-(2-aminophenylmethanesulfonylamino)-1H-azepane-2-carboxylic acid: Cal. 497.6 found (M)+ 498;

1-(4-Methoxy-benzenesulfonyl)-3-(phenylmethanesulfonylamino)-1H-azepane-2-carboxylic acid: Cal. 482.6 found (M)+ 483;

cis-1-(4-Methoxy-benzenesulfonyl)-3-(phenylmethanesulfonylamino)-heptamethyleneimine-2-carboxylic acid: Cal. 496.6 found (M–H)+ 495;

trans-1-(4-Methoxy-benzenesulfonyl)-3-(phenylmethanesulfonylamino)-heptamethyleneimine-2-carboxylic acid: Cal. 496.6 found (M–H)+ 495;

3-Benzyloxycarbonylamino-1-(4-methoxy-benzenesulfonyl)-1H-azepane-2-carboxylic acid: Cal. 462.52 found (M–H)+ 461.2;

1-(4-Methoxy-benzenesulfonyl)-3-(methanesulfonylamino)-2,3,4,7-tetrahydro-1H-azepine-2-carboxylic acid: Cal. 404.5 found (M)+ 405;

1-(4-Methoxy-benzenesulfonyl)-3-(phenylsulfonylamino)-2,3,4,7-tetrahydro-1H-azepine-2-carboxylic acid: Cal. 466.6 found (M)+ 467;

1-(4-Methoxy-benzenesulfonyl)-3-(2-napthylsulfonylamino)-2,3,4,7-tetrahydro-1H-azepine-2-carboxylic acid: Cal. 516.6 found (M)+ 517:

1-(4-Methoxy-benzenesulfonyl)-3-(1-napthylsulfonylamino)-2,3,4,7-tetrahydro-1H-azepine-2-carboxylic acid: Cal. 516.6 found (M)+ 517;

1-(4-Chlorophenyl-phenylsulfonyl)-3-(phenylmethanesulfonylamino)-2,3,4,7-tetrahydro-1H-azepine-2-carboxylic acid: Cal. 560.6 found (M)+ 561;

1-(4-Methoxy-benzenesulfonyl)-3-(4-Chlorophenyl-phenylsulfonylamino)-2,3,4,7-tetrahydro-1H-azepine-2-carboxylic acid: Cal. 577.1 found (M)+ 577;

1-(4-Methoxy-benzenesulfonyl)-3-(2-nitrophenyl-methanesulfonylamino)-2,3,4,7-tetrahydro-1H-azepine-2-carboxylic acid: Cal. 525.6 found (M)+ 526;

1-(4-Methoxy-benzenesulfonyl)-3-(phenylacroylsulfonylamino)-2,3,4,7-tetrahydro-1H-azepine-2-carboxylic acid: Cal. 492.6 found (M)+ 493;

1-(4-Methoxy-benzenesulfonyl)-3-(4-iodophenylsulfonylamino)-2,3,4,7-tetrahydro-1H-azepine-2-carboxylic acid: Cal. 592.7 found (M–H)+ 593;

1-(4-Methoxy-benzenesulfonyl)-3-(acetylamino)-2,3,4,7-tetrahydro-1H-azepine-2-carboxylic acid: Cal. 368.4 found (M)+ 369;

1-(4-Methoxy-benzenesulfonyl)-3-(2-thiophene-2-acetylamino)-2,3,4,7-tetrahydro-1H-azepine-2-carboxylic acid: Cal. 450.5 found (M)+ 451;

3-(3-Phenethylureido)-1-(4-methoxy-benzenesulfonyl)-2,3,4,7-tetrahydro-1H-azepine-2-carboxylic acid: Cal. 473.5 found (M)+ 474;

3-(3-Methylureido)-1-(4-methoxy-benzenesulfonyl)-2,3,4,7-tetrahydro-1H-azepine-2-carboxylic acid: Cal. 383.4 found (M)+ 384;

3-(3-Phenylureido)-1-(4-methoxy-benzenesulfonyl)-2,3,4,7-tetrahydro-1H-azepine-2-carboxylic acid: Cal. 445.5 found (M)+ 446;

3-(3,3-Benzylmethylureido)-1-(4-methoxy-benzenesulfonyl)-2,3,4,7-tetrahydro-1H-azepine-2-carboxylic acid: Cal. 473.5 found (M)+ 474;

3-(3,3-Benzylphenylureido)-1-(4-methoxy-benzenesulfonyl)-2,3,4,7-tetrahydro-1H-azepine-2-carboxylic acid: Cal. 535.6 found (M)+ 536;

3-Methoxycarbonylamino-1-(4-methoxy-benzenesulfonyl)-2,3,4,7-tetrahydro-1H-azepine-2-carboxylic acid: Cal. 384.41 found (M)+ 385;

3-(4-Trifluoromethylbenzyloxycarbonylamino)-1-(4-methoxy-benzenesulfonyl)-2,3,4,7-tetrahydro-1H-azepine-2-carboxylic acid: Cal. 528.5 found (M)+ 529;

3-(4-Chlorobenzyloxycarbonylamino)-1-(4-methoxy-benzenesulfonyl)-2,3,4,7-tetrahydro-1H-azepine-2-carboxylic acid: Cal. 494.9 found (M)+ 495;

3-(3,5-Dichlorobenzyloxycarbonylamino)-1-(4-methoxy-benzenesulfonyl)-2,3,4,7-tetrahydro-1H-azepine-2-carboxylic acid: Cal. 529.4 found (M)+ 530.

EXAMPLE 12

Using the procedures of the above general descriptions and the above examples, the compounds of Table I can be prepared.

TABLE I

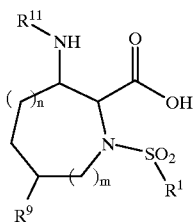

| R¹ | R⁹ | n | m | R¹¹ |
|---|---|---|---|---|
| 4-ClPh—Ph | H | 0 | 1 | PhCH₂SO₂ |
| 4-ClPh—Ph | OH | 0 | 1 | PhCH₂SO₂ |
| 4-ClPh—Ph | OMe | 0 | 2 | PhCH₂OCO |
| 4-ClPh—Ph | Ph | 1 | 1 | PhCH₂OCO |
| 4-ClPh—Ph | PyrCH₂ | 0 | 1 | PhCH₂SO₂ |
| 4-MeOPh—Ph | H | 0 | 1 | PhCH₂SO₂ |
| 4-MeOPh—Ph | OH | 0 | 1 | PhCH₂SO₂ |
| 4-MeOPh—Ph | OMe | 0 | 2 | PhCH₂OCO |
| 4-MeOPh—Ph | Ph | 1 | 1 | PhCH₂OCO |
| 4-MeOPh—Ph | PyrCH₂ | 0 | 1 | PhCH₂SO₂ |
| 4-Ph-4-piperidine-4-Ph | H | 0 | 1 | PhCH₂SO₂ |
| 4-Ph-4-piperidine-4-Ph | OH | 0 | 1 | PhCH₂SO₂ |
| 4-Ph-4-piperidine-4-Ph | OMe | 0 | 2 | PhCH₂OCO |
| 4-Ph-4-piperidine-4-Ph | Ph | 1 | 1 | PhCH₂OCO |
| 4-Ph-4-piperidine-4-Ph | PyrCH₂ | 0 | 1 | PhCH₂SO₂ |
| 4-benzoamidoPh | H | 0 | 1 | PhCH₂SO₂ |
| 4-benzoamidoPh | OH | 0 | 1 | PhCH₂SO₂ |
| 4-benzoamidoPh | OMe | 0 | 2 | PhCH₂OCO |
| 4-benzoamidoPh | Ph | 1 | 1 | PhCH₂OCO |
| 4-benzoamidoPh | PyrCH₂ | 0 | 1 | PhCH₂SO₂ |
| 4-pyridyl-oxyPh | H | 0 | 1 | PhCH₂SO₂ |
| 4-pyridyl-oxyPh | OH | 0 | 1 | PhCH₂SO₂ |
| 4-pyridyl-oxyPh | OMe | 0 | 2 | PhCH₂OCO |
| 4-pyridyl-oxyPh | Ph | 1 | 1 | PhCH₂OCO |
| 4-pyridyl-oxyPh | PyrCH₂ | 0 | 1 | PhCH₂SO₂ |

EXAMPLE 13

The following assays are in vitro assays which were used to characterize the ability of compounds of this invention to inhibit collagenase and stromelysin: Human Neutrophil Collagenase Assay and Human Fibroblast Stromelysin Assay.

Human Neutrophil Collagenase Assay

Human neutrophil collagenase (HNC) activity is determined by using fluorogenic peptide substrate Dnp-Pro-b-Cyclohexyl-Ala-Gly-Cys (Me)-His-Ala-Lys-(N-ethylanthranilic acid)-NH₂. The N-terminus Dnp group and the C-terminus N-methyl-anthranilyl moiety (Nma) are fluorescence self-quenching until the peptide is cleaved at the Gly-Cys(me) bond. The fluorescence from the cleavage products is measured on a Bio-Tek Instrument FL500 fluorescence micro-plate reader (excitation at 360 nm, emission at 460 nm). The assay is performed in a 96-well plate (in duplicate), and the Km=51 nM for the substrate, and Ki=722 nM for Actinonin have been determined. The test compounds (at 100, 33 & 10 mm) are compared for their inhibition of HNC activity on the substrate against the activity of Actinonin and Ki's were determined on selected compounds.

Human Fibroblast Stromelysin Assay

Human fibroblast stromelysin (HFS) activity is determined by using fluorogenic peptide substrate Dnp-Pro-b-Cyclohexyl-Ala-Gly-Cys (Me)-His-Ala-Lys-(N-methylanthranilic acid)-NH₂. The N-terminus Dnp group and the C-terminus N-methyl-anthranilyl moiety (Nma) are fluorescence self-quenching until the peptide is cleaved at the Gly-Cys(me) bond. The fluorescence from the cleavage products is measured on a Bio-Tek Instrument FL500 fluorescence micro-plate reader (excitation at 360 nm, emission at 460 nm). The assay is performed in a 96-well plate (in duplicate), and the Km=51 nM for the substrate, and Ki=722 nM for Actinonin (an inhibitor of enzyme activity; Sigma Chemical, St. Louis, Mo.; A6671) have been determined as the standard control. The test compounds (at 100, 33 & 10 mm) are compared for their inhibition of HFS activity on-the substrate against the activity of Actinonin and Ki's were determined on selected compounds.

The following compounds had a HNC and/or HFS inhibition activity $IC_{50}$ of less than 10 $\mu M$:

1-(4-Methoxy-benzenesulfonyl)-3-(2-aminophenylmethanesulfonylamino)-1H-azepane-2-carboxylic acid;

1-(4-Methoxy-benzenesulfonyl)-3-(phenylmethanesulfonylamino)-1H-azepane-2-carboxylic acid;

1-(4-Chlorophenyl-phenylsulfonyl)-3-(phenylmethanesulfonylamino)-2,3,4,7-tetrahydro-1H-azepine-2-carboxylic acid;

1-(4-Methoxy-benzenesulfonyl)-3-(2-nitrophenyl-methanesulfonylamino)-2,3,4,7-tetrahydro-1H-azepine-2-carboxylic acid;

1-(4-Methoxy-benzenesulfonyl)-3-(phenylacroylsulfonylamino)-2,3,4,7-tetrahydro-1H-azepine-2-carboxylic acid;

3-(4-Chlorobenzyloxycarbonylamino)-1-(4-methoxy-benzenesulfonyl)-2,3,4,7-tetrahydro-1H-azepine-2-carboxylic acid;

3-(3,5-Dichlorobenzyloxycarbonylamino)-1-(4-methoxy-benzenesulfonyl)-2,3,4,7-tetrahydro-1H-azepine-2-carboxylic acid.

Methods of Treatment

All of the compounds of this invention are useful in the prophylaxis and treatment of disease states in which HNC and/or HFS and/or gelatinases play a role. Preferably, the compounds of this invention are useful in the prophylaxis and treatment of rheumatoid arthritis; osteoarthritis; osteopenias (e.g., osteoporosis); periodontitis; gingivitis; corneal, epidermal and gastric ulceration; and tumour metastasis, invasion and growth; in neuroinflammatory disorders, such as myelin degradation (e.g., multiple sclerosis); and in angiogenesis dependent diseases, such as arthritic conditions; cancer; solid tumor growth; psoriasis; proliferative retinopathies; neovascular glaucoma; ocular tumours; angiofibromas; hemangiomas; nephritis; pulmonary inflammation; and restenosis.

The present invention provides a method of treating a disease state in which HNC and/or HFS and/or gelatinases levels are elevated which comprises administering an effective amount of a compound of this invention. Compounds of this invention are of use in the prophylaxis and acute or chronic therapy of any disease state in a human, or other mammal, which may contribute to the onset or etiology of, is exacerbated by or mediated by elevated or unregulated HNC and/or HFS and/or gelatinase by mammal's cells. More preferably, this invention relates to a method of lowering the activity levels of HNC and/or HFS and/or gelatinases in a mammal in need thereof which comprises administering an effective dose of a compound of this invention or a pharmaceutical composition thereof.

A compound of this invention or a pharmaceutical composition-thereof is useful in the treatment or prophylaxis of a number of disease states including rheumatoid arthritis; osteoarthritis; osteopenias (e.g., osteoporosis); periodontitis; gingivitis; corneal, epidermal and gastric ulceration; and tumour metastasis, invasion and growth; in neuroinflammatory disorders, such as myelin degradation (e.g., multiple sclerosis); and in angiogenesis dependent diseases, such as arthritic conditions; cancer; solid tumor growth; psoriasis; proliferative retinopathies; neovascular glaucoma; ocular tumours; angiofibromas; hemangiomas; nephritis; pulmonary inflammation; and restenosis.

Pharmaceutical Compositions

This invention further relates to the use of a compound of this invention in the manufacture of a edicament for the prophylaxis and treatment, either acutely or chronically, of disease states in which HNC and/or HFS and/or gelatinases play a role.

This invention also relates to a pharmaceutical composition comprising a compound of this invention and a pharmaceutically acceptable carrier, and if desired other active ingredients. The compounds of this invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art.

For the prophylaxis and treatment of disease states, the compounds of the present invention may be administered orally, parentally, or by inhalation spray, rectally, or topically in dosage unit formulations containing conventional pharmaceutically acceptable carriers, adjuvants and vehicles. The term parenteral as used herein includes, subcutaneous, intravenous, intramuscular, intrasternal, infusion techniques or intraperitoneally.

The amount of active ingredient that may be combined with the carrier materials to produce a single dosage form will vary depending upon the host treated and the particular mode of administration.

The dosage regimen for treating a disease state with the compounds of this invention and/or compositions of this invention is based on a variety of factors, including the type of disease, the age, weight, sex and medical condition of the patient, the severity of the condition, the route of administration, pharmacological considerations such as the activity, efficacy, pharmacokinetic and toxicology profiles of the particular compound employed, whether a drug delivery system is utilized and whether the compound is administered as part of a drug combination. Thus the dosage regimen may vary widely. Dosage levels of the order from about 0.01 mg to 80 mg per kilogram of body weight per day, preferably from about 0.5 mg to 30 mg/kg, more preferably from about 1 mg to 15 mg/kg are useful for all methods of use disclosed herein. The pharmaceutically active compounds of this invention can be processed in accordance with conventional methods of pharmacy to produce medicinal agents for administration to patients, mammals including humans.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 250 mg, preferably from about 25 to 150 mg. A suitable daily dose for a human or other mammal may vary widely depending on the condition of the patient and other factors.

The compounds of this invention may also be administered by injection as a composition with suitable carriers including saline, dextrose, or water. The daily parenteral dosage regimen will be from about 0.1 to about 80 mg/kg of total body weight, preferably from about 0.5 to about 30 mg/kg, and more preferably from about 1 mg to 15 mg/kg.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

A suitable topical dose of compounds of this invention is 0.1 mg to 150 mg administered one to four, preferably two or three times daily. For topical administration, the active ingredient may comprise from 0.001% to 10% w/w, e.g. from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin such as liniments, lotions, ointments, creams, or pastes and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, sodium, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, benzyl alcohol, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form including granules, powders or suppositories or in a liquid form such as solutions, suspensions, or emulsions. The pharmaceutical compositions may be subjected to conventional pharmaceutical operations such as sterilization and/or may contain conventional adjuvants, such as preservatives, stabilizers, wetting agents, emulsifiers, buffers, etc.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more other agents. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula

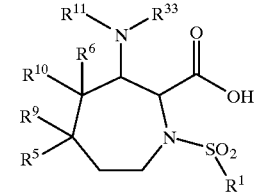

or a pharmaceutically acceptable salt thereof, wherein $R^1$ is (1) an alkyl, alkenyl, alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, alkanoylamino, alkylsulfonylamino, alkoxycarbonylamino, alkoxycarbonyl, cyano, halo, azido, alkyl or haloalkyl; provided that the total number of phenyl, aryl, heteroaryl, cycloalkyl and heterocyclyl radicals in R$^1$ is 0–3;

wherein each R$^3$ is independently an alkyl, haloalkyl, aryl, heteroaryl, aryl-alkyl or heteroaryl-alkyl radical, wherein the aryl and heteroaryl radicals are optionally substituted by 1–3 radicals of hydroxy, alkoxy, alkylthiol, amino, alkanoylamino, alkylsulfonylamino, alkylsulfinyl, alkylsulfonyl, alkoxycarbonylamino, alkoxycarbonyl, cyano, halo, azido, alkyl, haloalkyl or haloalkoxy; and each $R^4$ is independently a hydrogen or alkyl radical;

$R^{11}$ is a —C(O)—$R^{31}$, —C(O)—$OR^{30}$, —C(O)—$NR^{32}R^{31}$, —S(O)$_2$—$R^{30}$ or —S(O)$_2$—$NR^{32}R^{31}$ radical;

$R^5$ and $R^6$ are each independently a hydrogen or alkyl radical; or $CR^5$—$CR^6$ is C=C;

wherein $R^9$ and $R^{10}$ are each independently —B—A, provided that the combined total number of aryl, heteroaryl, cycloalkyl and heterocyclyl radicals in $R^9$, $R^{10}$ and $R^{11}$ is 0–3;

wherein each B is independently a
- (1) bond;
- (2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio, cyano or halo, and/or (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy;
- (3) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl, haloalkyl or haloalkoxy; or
- (4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, haloalkyl or haloalkoxy;

each A is independently a
- (1) hydrogen radical;
- (2) halo, cyano or nitro radical;
- (3) —C(O)—$R^{30}$, —C(O)—$OR^{31}$, —C(O)—$NR^{32}R^{31}$ or —C($NR^{32}$)—$NR^{32}R^{31}$ radical;
- (4) —$OR^{31}$, —O—C(O)—$R^{31}$, —O—C(O)—$NR^{32}R^{31}$ or —O—C(O)—$NR^{33}$—S(O)$_2$—$R^+$ radical;
- (5) —$SR^{31}$, —S(O)—$R^{30}$, —S(O)$_2$—$R^{30}$, —S(O)$_2$—$NR^{32}R^{31}$, —S(O)$_2$—$NR^{33}$—C(O)—$R^{31}$, —S(O)$_2$—$NR^{33}$—C(O)—$OR^{30}$ or —S(O)$_2$—$NR^{33}$—C(O)—$NR^{32}R^-$radical; or
- (6) —$NR^{32}R^{31}$, —$NR^{33}$—C(O)—$R^{31}$, —$NR^{33}$—C(O)—$OR^{30}$, —$NR^{33}$—C(O)—$NR^{32}R^{31}$ —$NR^{33}$—C($NR^{32}$)—$NR^{32}R^{31}$, —$NR^{33}$—S(O)$_2$—$R^{30}$ or —$NR^{33}$—S(O)$_2$—$NR^{32}R^{31}$ radical;

wherein each $R^{30}$ is independently
- (1) alkyl, alkenyl or alkynyl radical optionally substituted by 1–3 radicals of —$CO_2R^{34}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, cyano, halo or aralkoxy, arylalkylthio, arylalkylsulfonyl, cycloalkyl, heterocyclyl, aryl or heteroaryl radicals, wherein the cycloalkyl, heterocyclyl, aryl and heteroaryl radicals are optionally substituted by 1–3 radicals of amino, alkylamino, dialkylamino, alkanoylamino, alkoxycarbonylamino, alkylsulfonylamino, alkanoyl, alkoxycarbonyl, hydroxy, alkoxy, alkylthio, alkylsulfinyl, alkylsulfonyl, cyano, halo, alkyl, haloalkyl or haloalkoxy;
- (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl, haloalkyl or haloalkoxy; or
- (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl, haloalkyl or haloalkoxy;

each $R^{31}$ is independently hydrogen radical or $R^{30}$;

wherein each $R^{32}$ is independently
- (1) hydrogen radical;
- (2) alkyl, alkenyl or alkynyl radical optionally substituted by 1–3 radicals of amino, alkylamino, dialkylamino, hydroxy, alkoxy, alkylthio, cyano or halo; or
- (3) aryl, heteroaryl, arylalkyl, heteroarylalkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, cyano, alkyl, haloalkyl or haloalkoxy; and each $R^{33}$ is independently
- (1) hydrogen radical;
- (2) alkyl radical optionally substituted by a radical of heterocyclyl, aryl or heteroaryl which is optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy; or
- (3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy; and each $R^{34}$ is independently hydrogen, alkyl, aryl, heteroaryl, arylalkyl or heteroarylalkyl radical, wherein the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl, haloalkyl or haloalkoxy.

2. The compound of claim 1 or a pharmaceutically acceptable salt thereof, wherein $R^1$ is (1) an $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH, —$OR^3$, —$SR^3$, —S(O)$R^3$, —S(O)$_2R^3$, —C(O)$R^3$, —$NR^3R^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)R^3$, —$S(O)_2R^3$, —$C(O)R^3$, —$NR^3R^4$, amino, $C_1$–$C_8$ alkanoylamino, $C_1$–$C_8$ alkylsulfonylamino, $C_1$–$C_8$ alkoxycarbonylamino, $C_1$–$C_8$ alkoxycarbonyl, cyano, halo, azido, $C_1$–$C_8$ alkyl or $C_1$–$C_8$ haloalkyl of 1–3 halo radicals; provided that the total number of phenyl, aryl, heteroaryl, cycloalkyl and heterocyclyl radicals in $R^1$ is 0–3;

wherein each $R^3$ is independently a $C_1$–$C_8$ alkyl, $C_1$–$C_8$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_8$ alkanoylamino, $C_1$–$C_8$ alkylsulfonylamino, $C_1$–$C_4$ alkylsulfinyl, $C_1$–$C_4$ alkylsulfonyl, $C_1$–$C_8$ alkoxycarbonylamino, $C_1$–$C_8$ alkoxycarbonyl, cyano, halo, azido, $C_1$–$C_8$ alkyl, $C_1$–$C_8$ haloalkyl of 1–3 halo radicals or $C_1$–$C_8$ haloalkoxy of 1–3 halo radicals; and each $R^4$ is independently a hydrogen or $C_1$–$C_8$ alkyl radical;

$R^{11}$ is a —$C(O)$—$R^{31}$, —$C(O)$—$OR^{30}$, —$C(O)$—$NR^{32}R^{31}$, —$S(O)_2$—$R^{30}$ or —$S(O)_2$—$NR^{32}R^{31}$ radical;

$R^5$ and $R^6$ are each independently a hydrogen or $C_1$–$C_4$ alkyl radical; or $CR^5$–$CR^6$ is C=C;

wherein $R^9$ and $R^{10}$ are each independently —B—A, provided that the combined total number of aryl, heteroaryl, cycloalkyl and heterocyclyl radicals in $R^9$, $R^{10}$ and $R^{11}$ is 0–3;

wherein each B is independently a
(1) bond;
(2) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano or halo, and/or (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;
(3) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or
(4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_8$ haloalkyl of 1–3 halo radicals or $C_1$–$C_8$ haloalkoxy of 1–3 halo radicals;

each A is independently a
(1) hydrogen radical;
(2) halo, cyano or nitro radical;
(3) —$C(O)$—$R^{30}$, —$C(O)$—$OR^{31}$, —$C(O)$—$NR^{32}R^{31}$ or —$C(NR^{32})$—$NR^{32}R^{31}$ radical;
(4) —$OR^{31}$, —O—$C(O)$—$R^{31}$, —O—(O)—$NR^{32}R^{31}$ or —O—$C(O)$—$NR^{33}$—$S(O)_2$—$R^{30}$ radical;
(5) —$SR^{31}$, —$S(O)$—$R^{30}$, —$S(O)_2$—$R^{30}$, —$S(O)_2$—$NR^{32}R^{31}$, —$S(O)_2$—$NR^{33}$—$C(O)$—$R^{31}$, —$S(O)_2$—$NR^{33}$—$C(O)$—$OR^{30}$ or —$S(O)_2$—$NR^{33}$—$C(O)$—$NR^{32}R^{31}$ radical; or
(6) —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$C(NR^{32})$—$NR^{32}R^{31}$, —$NR^{33}$—$S(O)_2$—$R^{30}$ or —$NR^{32}$—$S(O)_2$—$NR^{32}R^{31}$ radical;

wherein each $R^{30}$ is independently
(1) $C_1$–$C_8$ alkyl, $C_2$–$C_8$ alkenyl or $C_2$–$C_8$ alkynyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy) carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

each $R^{31}$ is independently hydrogen radical or $R^{30}$;

wherein each $R^{32}$ is independently
(1) hydrogen radical;
(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; and each $R^{33}$ is independently
(1) hydrogen radical;
(2) $C_1$–$C_4$ alkyl radical optionally substituted by a radical of heterocyclyl, aryl or heteroaryl which is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; or (3) heterocyclyl, aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; and each $R^{34}$ is independently hydrogen or $C_1$–$C_4$ alkyl, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals; and wherein cycloalkyl is a monocyclic, bicyclic or tricyclic carbocyclic alkyl radical of 3–10 ring members, which is optionally partially unsaturated or benzo-fused; heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl, biphenyl or naphthyl radical; and heteroaryl is a radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein $R^1$ is (1) a $C_1$–$C_{12}$ alkyl, $C_2$–$C_{12}$ alkenyl, $C_2$–$C_{12}$ alkynyl, cycloalkyl or heterocyclyl radical optionally substituted by 1–3 radicals of —OH, —OR$^3$, —SR$^3$, —S(O)R$^3$, —S(O)$_2$R$^3$, —C(O)R$^3$, —NR$^3$R$^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —OR$^3$, —SR$^3$, —S(O)R$^3$, —S(O)$_2$R$^3$, —C(O)R$^3$, —NR$^3$R$^4$, amino, $C_1$–$C_4$ alkanoylamino, $C_1$–$C_4$ alkylsulfonylamino, $C_1$–$C_4$ alkoxycarbonylamino, $C_1$–$C_4$ alkoxycarbonyl, cyano, halo, azido, $C_1$–$C_6$ alkyl or $C_1$–$C_4$ haloalkyl of 1–3 halo radicals; provided that the total number of phenyl, aryl, heteroaryl, cycloalkyl and heterocyclyl radicals in $R^1$ is 0–3;

wherein each $R^3$ is independently a $C_1$–$C_4$ alkyl, $C_1$–$C_4$ haloalkyl of 1–3 halo radicals, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, $C_1$–$C_4$ alkanoylamino, $C_1$–$C_4$ alkylsulfonylamino, $C_1$–$C_4$ alkylsulfinyl, $C_1$–$C_4$ alkylsulfonyl, $C_1$–$C_4$ alkoxycarbonylamino, $C_1$–$C_4$ alkoxycarbonyl, cyano, halo, azido, $C_1$–$C_4$ alkyl, $C_1$–$C_4$ haloalkyl of 1–3 halo radicals or $C_1$–$C_4$ haloalkoxy of 1–3 halo radicals; and each $R^4$ is independently a hydrogen or $C_1$–$C_4$ alkyl radical;

wherein each B is independently a (1) bond;

(2) $C_1$–$C_8$ alkyl radical optionally substituted by (a) a radical of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;

(3) heterocyclyl radical; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, $C_1$–$C_4$ haloalkyl of 1–3 halo radicals or $C_1$–$C_4$ haloalkoxy of 1–3 halo radicals;

wherein each $R^{30}$ is independently (1) $C_1$–$C_6$ alkyl radical optionally substituted by 1–3 radicals of —CO$_2$R$^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, $C_1$–$C_4$ haloalkyl of 1–3 halo radicals or $C_1$–$C_4$ haloalkoxy of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_4$ haloalkyl of 1–3 halo radicals or $C_1$–$C_4$ haloalkoxy of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl, $C_1$–$C_4$ haloalkyl of 1–3 halo radicals or $C_1$–$C_4$ haloalkoxy of 1–3 halo radicals;

each $R^{31}$ is independently hydrogen radical or $R^{30}$;

wherein each $R^{32}$ is independently hydrogen or $C_1$–$C_4$ alkyl radical;

each $R^{33}$ is independently hydrogen or $C_1$–$C_4$ alkyl radical; and each $R^{34}$ is independently hydrogen or $C_1$–$C_4$ alkyl radical.

4. The compound of claim 3 or a pharmaceutically acceptable salt thereof, wherein $R^1$ is (1) a $C_1$–$C_{12}$ alkyl radical optionally substituted by 1–3 radicals of —OH, —$OR^3$, —$SR^3$, —$S(O)R^3$, —$S(O)_2R^3$, —$C(O)R^3$, —$NR^3R^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)R^3$, —$S(O)_2R^3$, —$C(O)R^3$, —$NR^3R^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —$CF_3$ radicals; provided that the total number of phenyl, aryl, heteroaryl, cycloalkyl and heterocyclyl radicals in $R^1$ is 0–3;

wherein each $R^3$ is independently an $C_1$–$C_4$ alkyl, —$CF_3$, aryl, heteroaryl, aryl-$C_1$–$C_4$-alkyl or heteroaryl-$C_1$–$C_4$-alkyl radical, wherein the aryl and heteroaryl radicals are optionally substituted by 1–3 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —$CF_3$ or —$OCF_3$; and each $R^1$ is independently a hydrogen or methyl radical;

wherein each B is independently a (1) bond;

(2) $C_1$–$C_8$ alkyl radical optionally substituted by (a) a radical of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, and/or (b) 1–3 halo radicals, and/or (c) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

(3) heterocyclyl radical; or (4) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

each A is independently a (1) hydrogen radical;

(2) halo, cyano or nitro radical;

(3) —$C(O)$—$R^{30}$, —$C(O)$—$OR^{31}$, —$C(O)$—$NR^{32}R^{31}$ or —$C(NR^{32})$—$NR^{32}R^{31}$ radical;

(4) —$OR^{31}$, —$O$—$C(O)$—$R^{31}$ or —$O$—$C(O)$—$NR^{32}R^{31}$ radical;

(5) —$SR^{31}$, —$S(O)$—$R^{31}$, —$S(O)_2$—$R^{30}$ or —$S(O)_2$—$NR^{32}R^{31}$ radical; or (6) —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$C(NR^{32})$—$NR^{32}R^{31}$, —$NR^{33}$—$S(O)_2$—$R^{30}$ or —$NR^{33}$—$S(O)_2$—$NR^{32}R^{31}$ radical;

wherein each $R^1$ is independently (1) $C_1$–$C_6$ alkyl radical optionally substituted by 1–3 radicals of —$CO_2R^{34}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl, —$CF_3$ or —$OCF_3$ radicals;

(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl, $C_1$–$C_2$ haloalkyl of 1–3 halo radicals or —$OCF_3$; or (3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl, —$CF_3$ or —$OCF_3$ radicals;

each $R^{31}$ is independently hydrogen radical or $R^{30}$; and each $R^{33}$ is independently a hydrogen or methyl radical.

5. The compound of claim 4 or a pharmaceutically acceptable salt thereof, wherein $R^{11}$ is a —$C(O)$—$R^{31}$ or —$S(O)_2$—$R^{30}$ radical; provided that the combined total number of aryl, heteroaryl, cycloalkyl and heterocyclyl radicals in $R^9$, $R^{10}$ and $R^{11}$ is 0–2.

6. The compound of claim 5 or a pharmaceutically acceptable salt thereof, wherein $R^1$ is (1) an $C_1$–$C_{12}$ alkyl radical optionally substituted by 1–3 radicals of —OH, —$OR^3$, —$SR^3$, —$S(O)_2R^3$, —$NR^3R^4$, aryl, heteroaryl, cycloalkyl or heterocyclyl; or (2) an aryl radical optionally substituted by an optionally substituted monocyclic heteroaryl or heterocyclyl radical of 5–6 ring members which is optionally substituted by a phenyl radical or monocyclic heteroaryl radical of 5–6 ring members; or (3) a heteroaryl radical optionally substituted by an optionally substituted phenyl or a monocyclic heteroaryl or heterocyclyl radical of 5–6 ring members which is optionally substituted by a phenyl radical or monocyclic heteroaryl radical of 5–6 ring members; wherein the phenyl, aryl, heteroaryl, cycloalkyl and heterocyclyl radicals of (1), (2) and (3) are optionally substituted by 1–3 radicals of hydroxy, —$OR^3$, —$SR^3$, —$S(O)_2R^3$, —$NR^3R^4$, amino, acetylamino, methylsulfonylamino, $C_1$–$C_4$ alkoxycarbonylamino, $C_1$–$C_4$ alkoxycarbonyl, cyano, halo, $C_1$–$C_6$ alkyl or —$CF_3$ radicals; provided that the total number of phenyl, aryl, heteroaryl, cycloalkyl and heterocyclyl radicals in $R^1$ is 0–2;

wherein each $R^3$ is independently a $C_1$–$C_4$ alkyl, —$CF_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_4$ alkoxy, $C_1$–$C_4$ alkylthiol, amino, acetylamino, methylsulfonylamino, $C_1$–$C_4$ alkylsulfonyl, $C_1$–$C_4$ alkoxycarbonylamino, $C_1$–$C_4$ alkoxycarbonyl, cyano, halo, $C_1$–$C_4$ alkyl, —$CF_3$ or —$OCF_3$;

wherein each B is independently a (1) bond;

(2) $C_1$–$C_4$ alkyl radical optionally substituted by (a) a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, hydroxy, $C_1$–$C_2$ alkoxy, and/or (b) 1–2 halo radicals, and/or (c) a radical of heterocyclyl, aryl or heteroaryl optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals;

(3) heterocyclyl radical; or (4) aryl or heteroaryl radical optionally substituted by 1–2 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals;

each A is independently a (1) hydrogen radical;

(2) halo radical;

(3) —$C(O)$—$R^{30}$, —$C(O)$—$OR^{31}$, —$C(O)$—$NR^{32}R^{31}$ or —$C(NR^{32})$—$NR^{32}R^{31}$ radical;

(4) —$OR^{31}$ radical;

(5) —$SR^{31}$, $S(O)_2$—$R^{30}$ or —$S(O)_2$—$NR^{32}R^{31}$ radical; or (6) —$NR^{32}R^{31}$, —$NR^{33}$—$C(O)$—$R^{31}$, —$NR^{33}$—$C(O)$—$OR^{30}$, —$NR^{33}$—$C(O)$—$NR^{32}R^{31}$, —$NR^{33}$—$S(O)_2$—$R^{30}$ or —$NR^{33}$—$S(O)_2$—$NR^{32}R^{31}$ radical;

wherein each $R^1$ is independently (1) —$CF_3$ or $C_1$–$C_4$ alkyl radical optionally substituted by 1–2 radicals of —$CO_2R^{34}$, amino, $C_1$–$C_2$ alkylamino, di-($C_1$–$C_2$ alkyl)amino, $C_1$–$C_2$ alkanoylamino, ($C_1$–$C_4$ alkoxy)carbonylamino, N—(($C_1$–$C_4$ alkoxy)carbonyl)-N—($C_1$–$C_4$ alkyl)amino, hydroxy, $C_1$–$C_4$ alkoxy, or aryl-$C_1$–$C_2$-alkoxy, heterocyclyl, aryl or heteroaryl radicals, wherein the heterocyclyl, aryl and heteroaryl radicals are optionally substituted by 1–3 radicals of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_5$ alkanoyl, ($C_1$–$C_4$ alkoxy)carbonyl, hydroxy, $C_1$–$C_4$ alkoxy, halo, $C_1$–$C_4$ alkyl, —$CF_3$ or —$OCF_3$ radicals;

(2) heterocyclyl radical optionally substituted by 1–2 radicals of ($C_1$–$C_4$ alkoxy)carbonyl, hydroxy or $C_1$–$C_4$ alkyl; or (3) aryl or heteroaryl radicals optionally substituted by 1–2 radicals of amino, $C_1$–$C_2$ alkylamino, di-($C_1$–$C_2$ alkyl)amino, $C_1$–$C_2$ alkanoylamino, hydroxy, $C_1$–$C_2$ alkoxy, halo, $C_1$–$C_4$ alkyl, —$CF_3$ or —$OCF_3$ radicals;

each $R^{31}$ is independently hydrogen radical or $R^{30}$; and wherein cycloalkyl is a monocyclic carbocyclic alkyl radical of 3–6 ring members, which is optionally partially unsaturated or benzo-fused; and heterocyclyl is a radical of a monocyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals.

7. The compound of claim 6 or a pharmaceutically acceptable salt thereof, wherein $R^1$ is (1) an $C_1$–$C_4$ alkyl radical substituted by 1–2 radicals of —OH, —$OR^3$, —$NR^3R^4$, aryl or heteroaryl; or (2) an aryl radical optionally substituted by a monocyclic heteroaryl radical of 5–6 ring members; or (3) a heteroaryl radical optionally substituted by a phenyl radical; wherein the phenyl, aryl and heteroaryl radicals of (1), (2) and (3) are optionally substituted by 1–2 radicals of hydroxy, —$OR^3$, —$SR^3$, —$S(O)_2R^3$, —$NR^3R^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —$CF_3$ radicals; provided that the total number of phenyl, aryl and heteroaryl radicals in $R^1$ is 0–2;

wherein each $R^3$ is independently a $C_1$–$C_4$ alkyl, —$CF_3$, aryl, heteroaryl, aryl-$C_1$–$C_2$-alkyl or heteroaryl-$C_1$–$C_2$-alkyl radical, wherein the aryl and heteroaryl radicals are optionally substituted by 1–2 radicals of hydroxy, $C_1$–$C_2$ alkoxy, $C_1$–$C_2$ alkylthiol, amino, acetylamino, methylsulfonylamino, $C_1$–$C_2$ alkylsulfonyl, $C_1$–$C_4$ alkoxycarbonylamino, $C_1$–$C_4$ alkoxycarbonyl, halo, $C_1$–$C_2$ alkyl, —$CF_3$ or —$OCF_3$;

wherein each B is independently a (1) bond;

(2) $C_1$–$C_4$ alkyl radical; or (3) aryl or heteroaryl radical optionally substituted by a radical of amino, $C_1$–$C_2$ alkylamino, di-($C_1$–$C_2$ alkyl)amino, $C_1$–$C_2$ alkanoylamino, ($C_1$–$C_4$ alkoxy)carbonylamino, $C_1$–$C_2$ alkylsulfonylamino, hydroxy, $C_1$–$C_2$ alkoxy, $C_1$–$C_2$ alkylthio, halo, $C_1$–$C_4$ alkyl, —$CF_3$ or —$OCF_3$ radicals;

each A is independently a (1) hydrogen radical;

(2) halo radical;

(3) —$C(O)$—$R^{30}$, —$C(O)$—$NR^{32}R^{31}$ or —$C(NR^{32})$—$NR^{32}R^{31}$ radical;

(4) —$OR^{31}$ radical;

(5) —$SR^{31}$, —$S(O)_2$—$R^{30}$ or —$S(O)_2$—$NR^{32}R^{31}$ radical; or (6) —$NR^{32}R^{31}$, —$NR^{33}$—$C(O)$—$R^{31}$ or —$NR^{33}$—$S(O)_2$—$R^{30}$ radical;

wherein each $R^{30}$ is independently (1) heterocyclyl radical optionally substituted by 1–2 radicals of ($C_1$–$C_4$ alkoxy)carbonyl, hydroxy or $C_1$–$C_4$ alkyl; or

53

(2) heteroaryl radicals optionally substituted by 1–2 radicals of amino, $C_1$–$C_2$ alkylamino, di-($C_1$–$C_2$ alkyl) amino, $C_1$–$C_2$ alkanoylamino, hydroxy, $C_1$–$C_2$ alkoxy, halo, $C_1$–$C_4$ alkyl, —$CF_3$ or —$OCF_3$ radicals; and each $R^{31}$ is independently hydrogen radical or (1) —$CF_3$ or $C_1$–$C_4$ alkyl radical optionally substituted by 1–2 radicals of hydroxy, $C_1$–$C_2$ alkoxy or aryl-$C_1$–$C_2$-alkoxy, aryl or heteroaryl radicals, wherein the aryl and heteroaryl radicals are optionally substituted by 1–2 radicals of amino, $C_1$–$C_2$ alkylamino, di-($C_1$–$C_2$ alkyl) amino, $C_1$–$C_2$ alkanoylamino, ($C_1$–$C_4$ alkoxy) carbonylamino, $C_1$–$C_5$ alkanoyl, ($C_1$–$C_4$ alkoxy) carbonyl, hydroxy, $C_1$–$C_4$ alkoxy, halo, $C_1$–$C_4$ alkyl, —$CF_3$ or —$OCF_3$ radicals; or (2) aryl or heteroaryl radical optionally substituted by 1–2 radicals of amino, $C_1$–$C_2$ alkylamino, di-($C_1$–$C_2$ alkyl) amino, $C_1$–$C_2$ alkanoylamino, hydroxy, $C_1$–$C_2$ alkoxy, halo, $C_1$–$C_4$ alkyl, —$CF_3$ or —$OCF_3$ radicals.

8. The compound of claim 7 or a pharmaceutically acceptable salt thereof, wherein $R^1$ is aryl or heteroaryl radicals optionally substituted by 1–2 radicals of hydroxy, —$OR^3$, —$SR^3$, —$S(O)_2R^3$, —$NR^3R^4$, amino, acetylamino, methylsulfonylamino, $C_1$–$C_4$ alkoxycarbonylamino, $C_1$–$C_4$ alkoxycarbonyl, halo, $C_1$–$C_6$ alkyl or —$CF_3$ radicals; provided that the total number of aryl and heteroaryl radicals in $R^1$ is 1–2;

wherein each $R^3$ is independently a $C_1$–$C_4$ alkyl, —$CF_3$, aryl, heteroaryl, arylmethyl or heteroarylmethyl radical;

wherein each B is independently a (1) bond;

(2) $C_1$–$C_4$ alkyl radical; or (3) aryl or heteroaryl radical;

each A is independently a (1) hydrogen radical;

(2) halo radical; or (3) —C(O)—$R^{30}$ or —C(O)—$NR^{32}R^{31}$ radical;

wherein each $R^{30}$ is independently a heterocyclyl radical optionally substituted by $C_1$–$C_4$ alkyl;

each $R^{31}$ is independently hydrogen radical or (1) —$CF_3$ or $C_1$–$C_4$ alkyl radical optionally substituted by 1–2 radicals of aryl or heteroaryl radicals; or (2) aryl or heteroaryl radical; and wherein each $R^{32}$ is independently a hydrogen or methyl radical.

9. The compound of claim 8 or a pharmaceutically acceptable salt thereof, wherein $R^1$ is an aryl radical optionally substituted by 1–2 radicals of hydroxy, —$OR^3$, —$S(O)_2R^3$, —$NR^3R^4$, amino, acetylamino, methylsulfonylamino, halo, $C_1$–$C_4$ alkyl

54 or —$CF_3$ radicals; provided that the total number of aryl and heteroaryl radicals in $R^1$ is 1–2;

$R^5$, $R^6$, $R^9$ and $R^{10}$ are each a hydrogen radical; or $CR^5$–$CR^6$ is C=C; and wherein heterocyclyl is a radical of pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl or its sulfoxide or sulfone derivative, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl or ethylenedioxyphenyl; aryl is a phenyl, biphenyl or naphthyl radical; and heteroaryl is a radical of imidazolyl, pyrrolyl, pyrazolyl, pyridyl, pyrazinyl, triazolyl, furyl, thienyl, oxazolyl, thiazolyl, indolyl, quinolinyl, isoquinolinyl, 5,6,7,8-tetrahydroquinolyl, 5,6,7,8-tetrahydroisoquinolinyl, quinoxalinyl, benzothiazolyl, β-carbolinyl, benzofuryl, benzimidazolyl or benzoxazolyl.

10. The compound of claim 9 or a pharmaceutically acceptable salt thereof, wherein $R^1$ is a phenyl or biphenyl radical optionally substituted by 1–2 radicals of hydroxy, —$OR^3$, —$S(O)_2R^3$, —$NR^3R^4$, amino, acetylamino, methylsulfonylamino, halo, $C_1$–$C_4$ alkyl or —$CF_3$ radicals; provided that the total number of aryl and heteroaryl radicals in $R^1$ is 1–2;

wherein each $R^3$ is independently an $C_1$–$C_4$ alkyl, —$CF_3$, phenyl, heteroaryl, phenylmethyl or heteroarylmethyl radical; and wherein heterocyclyl is a radical of pyrrolidinyl, piperidinyl, piperazinyl, morpholinyl, thiamorpholinyl, 4-benzyl-piperazin-1-yl or pyrimidinyl; and heteroaryl is a radical of imidazolyl, pyrrolyl, pyrazolyl, pyridyl, pyrazinyl, indolyl, quinolinyl, isoquinolinyl, benzothiazolyl, benzofuryl, benzimidazolyl or benzoxazolyl.

11. The compound of claim 10 or a pharmaceutically acceptable salt thereof, wherein $R^1$ is a phenyl or biphenyl radical optionally substituted by 1–2 radicals of hydroxy, —$OR^3$, halo, methyl or —$CF_3$ radicals; provided that the total number of aryl and heteroaryl radicals in $R^1$ is 1–2; and wherein each $R^3$ is independently an methyl, —$CF_3$, phenyl, heteroaryl, phenylmethyl or heteroarylmethyl radical.

12. A pharmaceutical composition comprising a compound of any one of claims 1–11 and a pharmaceutically acceptable carrier.

* * * * *

UNITED STATES PATENT AND TRADEMARK OFFICE
CERTIFICATE OF CORRECTION

PATENT NO. : 6,291,450 B1
DATED : September 18, 2001
INVENTOR(S) : Koch et al.

It is certified that error appears in the above-identified patent and that said Letters Patent is hereby corrected as shown below:

Column 9,
Line 41, change the first "alkylsulfonyl" to -- alkylsulfinyl --.

Column 17,
Line 5, delete "R—".

Column 19,
Line 28, change "9" to -- β --.

Column 30,
Line 20, change "2-Al lyl" to -- 2-Allyl --.

Column 34,
Line 37, change "benzenesilfonyl)" to -- benzenesulfonyl) --.

Column 37,
Line 48, change "ethylanthranilic" to -- methylanthranilic --.
Line 57, change "10 mm" to -- 10 mM --.

Column 38,
Line 10, change "10 mm" to -- 10 mM --.

Column 39,
Line 16, change "edicament" to -- medicament --.

Column 43,
Line 43, change "R$^+$" to R$^{30}$ --.
Line 48, change "NR$^{32}$"R$^-$" to -- NR$^{32}$R$^{31}$ --.

Column 46,
Line 10, change "—NR$^{32}$—S(O)$_2$" to -- —NR$^{33}$—S(O)$_2$ --.

Column 49,
Line 48, change "R$^1$" to -- R$^4$ --.

UNITED STATES PATENT AND TRADEMARK OFFICE
CERTIFICATE OF CORRECTION

PATENT NO. : 6,291,450 B1
DATED : September 18, 2001
INVENTOR(S) : Koch et al.

It is certified that error appears in the above-identified patent and that said Letters Patent is hereby corrected as shown below:

Column 50,
Line 12, change "$R^{31}$" to -- $R^{30}$ --.
Line 18, change "$R^{1}$" to -- $R^{30}$ --.

Column 51,
Line 57, change "$R^{1}$" to -- $R^{30}$ --.

Signed and Sealed this

Seventh Day of May, 2002

Attest:

Attesting Officer

JAMES E. ROGAN
Director of the United States Patent and Trademark Office